United States Patent
Cho et al.

(10) Patent No.: US 11,479,611 B2
(45) Date of Patent: Oct. 25, 2022

(54) HLA-G SPECIFIC CHIMERIC ANTIGEN RECEPTOR, NUCLEIC ACID, HLA-G SPECIFIC CHIMERIC ANTIGEN RECEPTOR EXPRESSION PLASMID, HLA-G SPECIFIC CHIMERIC ANTIGEN RECEPTOR EXPRESSING CELL, USE THEREOF, AND PHARMACEUTICAL COMPOSITION FOR TREATING CANCER

(71) Applicant: China Medical University Hospital, Taichung (TW)

(72) Inventors: Der-Yang Cho, Taichung (TW);
Shao-Chih Chiu, Taichung (TW);
Chia-Ing Jan, Taichung (TW);
Chih-Ming Pan, Taichung (TW);
Shi-Wei Huang, Taichung (TW)

(73) Assignee: China Medical University Hospital, Taichung (TW)

( * ) Notice: Subject to any disclaimer, the term of this patent is extended or adjusted under 35 U.S.C. 154(b) by 176 days.

(21) Appl. No.: 16/890,155

(22) Filed: Jun. 2, 2020

(65) Prior Publication Data
US 2021/0122825 A1    Apr. 29, 2021

(30) Foreign Application Priority Data

Oct. 24, 2019   (TW) .................................. 108138478

(51) Int. Cl.
| | | |
|---|---|---|
| C07K 16/28 | (2006.01) | |
| A61P 35/00 | (2006.01) | |
| C07K 16/30 | (2006.01) | |
| A61K 45/06 | (2006.01) | |
| A61K 39/00 | (2006.01) | |

(52) U.S. Cl.
CPC .......... *C07K 16/2833* (2013.01); *A61P 35/00* (2018.01); *C07K 16/30* (2013.01); *A61K 45/06* (2013.01); *A61K 2039/505* (2013.01); *C07K 2317/24* (2013.01); *C07K 2317/53* (2013.01); *C07K 2319/02* (2013.01); *C07K 2319/03* (2013.01)

(58) Field of Classification Search
CPC ................................................ C07K 16/2833; C07K 2317/24; A61K 45/06; A61K 2039/505
See application file for complete search history.

(56) References Cited

FOREIGN PATENT DOCUMENTS

| | | |
|---|---|---|
| CA | 2820681 A1 | 6/2012 |
| EP | 3623010 A1 | 8/2020 |
| JP | 2018509893 A | 4/2018 |
| JP | 2018511319 A | 4/2018 |
| WO | 2016127257 A1 | 8/2016 |
| WO | 2016160622 A2 | 10/2016 |
| WO | 2017120557 A1 | 7/2017 |
| WO | 2017222593 A1 | 12/2017 |
| WO | 2018057904 A1 | 3/2018 |
| WO | 2018091580 A1 | 5/2018 |
| WO | 2018237022 A1 | 12/2018 |

OTHER PUBLICATIONS

Sterner et al., CAR-T cell therapy: current limitations and potential strategies, Blood Cancer Journal, 2021, 11:69 (Year: 2021).*
Gura, T., Systems for Identifying New Drugs Are Often Faulty, Science, 1997, 278:1041-1042 (Year: 1997).*
Kaiser, J., First pass at cancer genoome reveals complex landscape, Science, 2006, 313:1370 (Year: 2006).*
Jena et al., Redirecting T-cell specificity by introducing a tumor-specific chimeric antigen receptor, Blood Aug. 19, 2010 116(7): 1035-1044 (Year: 2010).*
Oberschmidt, Olaf , et al., "Redirected Primary Human Chimeric Antigen Receptor natural Killer Cells as an "Off-the-Shelf immunotherapy" for improvement in Cancer Treatment", Frontiers in Immunology, Jun. 2017, vol. 8, Article 654, Jun. 9, 2017, 1-9.

* cited by examiner

*Primary Examiner* — Misook Yu
*Assistant Examiner* — Cheng Lu

(57) ABSTRACT

The present disclosure relates to a HLA-G specific chimeric antigen receptor, a nucleic acid, a HLA-G specific chimeric antigen receptor expression plasmid, a HLA-G specific chimeric antigen receptor expressing cell, a pharmaceutical composition for treating cancer, and use of the HLA-G specific chimeric antigen receptor expressing cell. The chimeric antigen receptor specifically binds to human leukocyte antigen G. The nucleic acid encodes the HLA-G specific chimeric antigen receptor. The HLA-G specific chimeric antigen receptor expression plasmid expresses the HLA-G specific chimeric antigen receptor. The HLA-G specific chimeric antigen receptor expressing cell is obtained by transducing the HLA-G specific chimeric antigen receptor into an immune cell. The pharmaceutical composition for treating cancer includes the HLA-G specific chimeric antigen receptor expressing cell and a pharmaceutically acceptable carrier.

16 Claims, 19 Drawing Sheets
Specification includes a Sequence Listing.

SEQUENCE LISTING

<160> NUMBER OF SEQ ID NOS: 18

<210> SEQ ID NO 1
<211> LENGTH: 246
<212> TYPE: PRT
<213> ORGANISM: Artificial Sequence
<220> FEATURE:
<223> OTHER INFORMATION: antigen recognition domain

<400> SEQUENCE: 1

```
Glu Val Gln Leu Gln Glu Ser Gly Gly Gly Leu Val Gln Pro Lys Gly
1               5                   10                  15

Ser Leu Lys Leu Ser Cys Ala Ala Phe Gly Phe Thr Phe Asn Thr Tyr
            20                  25                  30

Ala Met His Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Ser Leu Gln Met Asn Asn Leu Lys Thr Glu Asp Thr Ala Ile Tyr
                85                  90                  95

Tyr Cys Val Arg Gly Gly Tyr Trp Ser Phe Asp Val Trp Gly Ala Gly
            100                 105                 110

Thr Thr Val Thr Val Ser Ser Gly Gly Gly Ser Gly Gly Gly Gly
            115                 120                 125

Ser Gly Gly Gly Gly Ser Asp Ile Val Ile Thr Gln Thr Pro Ser
    130                 135                 140

Val Pro Val Thr Pro Gly Glu Ser Val Ser Ile Ser Cys Arg Ser Ser
145                 150                 155                 160

Lys Ser Leu Leu His Ser Asn Gly Asn Thr Tyr Leu Tyr Trp Phe Leu
            165                 170                 175

Gln Arg Pro Gly Gln Ser Pro Gln Leu Leu Ile Ser Arg Met Ser Ser
        180                 185                 190

Leu Ala Ser Gly Val Pro Asp Arg Phe Ser Gly Ser Gly Ser Gly Thr
    195                 200                 205

Ala Phe Thr Leu Arg Ile Ser Arg Val Glu Ala Glu Asp Val Gly Val
    210                 215                 220

Tyr Tyr Cys Met Gln His Leu Glu Tyr Pro Tyr Thr Phe Gly Gly Gly
225                 230                 235                 240

Thr Lys Leu Glu Ile Lys
                245
```

<210> SEQ ID NO 2
<211> LENGTH: 68
<212> TYPE: PRT
<213> ORGANISM: Artificial Sequence
<220> FEATURE:
<223> OTHER INFORMATION: transmembrane domain

<400> SEQUENCE: 2

```
Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45
```

```
Pro Thr Arg Lys His Tyr Gln Pro Tyr Ala Pro Pro Arg Asp Phe Ala
            50                  55                  60

Ala Tyr Arg Ser
65

<210> SEQ ID NO 3
<211> LENGTH: 94
<212> TYPE: PRT
<213> ORGANISM: Artificial Sequence
<220> FEATURE:
<223> OTHER INFORMATION: IL2 receptor zeta] chain signaling domain

<400> SEQUENCE: 3

Asn Cys Arg Asn Thr Gly Pro Trp Leu Lys Lys Val Leu Lys Cys Asn
1               5                   10                  15

Thr Pro Asp Pro Ser Lys Phe Phe Ser Gln Leu Ser Ser Glu His Gly
            20                  25                  30

Gly Asp Val Gln Lys Trp Leu Ser Ser Pro Phe Pro Ser Ser Ser Phe
        35                  40                  45

Ser Pro Gly Gly Leu Ala Pro Glu Ile Ser Pro Leu Glu Val Leu Glu
    50                  55                  60

Arg Asp Lys Val Thr Gln Leu Leu Pro Leu Asn Thr Asp Ala Tyr Leu
65                  70                  75                  80

Ser Leu Gln Glu Leu Gln Gly Gln Asp Pro Thr His Leu Val
                85                  90

<210> SEQ ID NO 4
<211> LENGTH: 112
<212> TYPE: PRT
<213> ORGANISM: Artificial Sequence
<220> FEATURE:
<223> OTHER INFORMATION: CD3 zeta signaling domain

<400> SEQUENCE: 4

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Tyr Arg His Gln Ala Leu Pro Pro
            100                 105                 110

<210> SEQ ID NO 5
<211> LENGTH: 21
<212> TYPE: PRT
<213> ORGANISM: Artificial Sequence
<220> FEATURE:
<223> OTHER INFORMATION: signal peptide

<400> SEQUENCE: 5

Met Ala Leu Pro Val Thr Ala Leu Leu Leu Pro Leu Ala Leu Leu Leu
1               5                   10                  15

His Ala Ala Arg Pro
```

```
<210> SEQ ID NO 6
<211> LENGTH: 8
<212> TYPE: PRT
<213> ORGANISM: Artificial Sequence
<220> FEATURE:
<223> OTHER INFORMATION: CDRH1

<400> SEQUENCE: 6

Gly Phe Thr Phe Asn Thr Tyr Ala
1               5

<210> SEQ ID NO 7
<211> LENGTH: 10
<212> TYPE: PRT
<213> ORGANISM: Artificial Sequence
<220> FEATURE:
<223> OTHER INFORMATION: CDRH2

<400> SEQUENCE: 7

Ile Arg Ser Lys Ser Asn Asn Tyr Ala Thr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: CDRH3

<400> SEQUENCE: 8

Val Arg Gly Gly Tyr Trp Ser Phe Asp Val
1               5                   10

<210> SEQ ID NO 9
<211> LENGTH: 11
<212> TYPE: PRT
<213> ORGANISM: Artificial Sequence
<220> FEATURE:
<223> OTHER INFORMATION: CDRL1

<400> SEQUENCE: 9

Lys Ser Leu Leu His Ser Asn Gly Asn Thr Tyr
1               5                   10

<210> SEQ ID NO 10
<211> LENGTH: 9
<212> TYPE: PRT
<213> ORGANISM: Artificial Sequence
<220> FEATURE:
<223> OTHER INFORMATION: CDRL3

<400> SEQUENCE: 10

Met Gln His Leu Glu Tyr Pro Tyr Thr
1               5

<210> SEQ ID NO 11
<211> LENGTH: 45
<212> TYPE: PRT
<213> ORGANISM: Artificial Sequence
<220> FEATURE:
<223> OTHER INFORMATION: CD8 hinge region

<400> SEQUENCE: 11

Thr Thr Thr Pro Ala Pro Arg Pro Pro Thr Pro Ala Pro Thr Ile Ala
1               5                   10                  15
```

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 12
<211> LENGTH: 738
<212> TYPE: DNA
<213> ORGANISM: Artificial Sequence
<220> FEATURE:
<223> OTHER INFORMATION: antigen recognition domain coding fragment

<400> SEQUENCE: 12
gaggttcagc tgcaagagtc tggcggagga ctggtgcagc taagggaag cctgaagctg      60 agctgtgccg ccttcggctt caccttcaac acctacgcca tgcactgggt ccgacaggcc     120
cctggaaaag gccttgaatg ggtcgcccgg atcagaagca agagcaacaa ttacgccacc     180
tactacgccg acagcgtgaa ggacagattc accatcagcc gggacgacag ccagagcatg     240
ctgagcctgc agatgaacaa cctgaaaacc gaggacaccg ccatctacta ctgcgtcaga     300
ggcggctact ggtccttcga tgtttgggga gccggcacca ccgtgacagt ttctagcgga     360
ggcggtggat ctggcggcgg aggaagtggt ggcggaggtt ctgatatcgt gatcacccag     420
accacaccta gcgtgccagt gacacctggc gagagcgtgt ccatcagctg cagaagcagc     480
aagagcctgc tgcacagcaa cggcaatacc tacctgtact ggttcctgca gaggcccgga     540
cagtctcctc agctgctgat ctccagaatg agcagcctgg ctagcggcgt gcccgataga     600
ttttctggca gcggctctgg caccgccttc acactgagaa tcagcagagt ggaagccgag     660
gacgtgggcg tgtactactg tatgcagcac ctggaatacc cctacacctt cggcggaggc     720
accaagctgg aaatcaag                                                    738

<210> SEQ ID NO 13
<211> LENGTH: 204
<212> TYPE: DNA
<213> ORGANISM: Artificial Sequence
<220> FEATURE:
<223> OTHER INFORMATION: transmembrane domain coding fragment

<400> SEQUENCE: 13
ttttgggtgc tggtggtggt tggtggagtc ctggcttgct atagcttgct agtaacagtg      60
gcctttatta ttttctgggt gaggagtaag aggagcaggc tcctgcacag tgactacatg     120
aacatgactc cccgccgccc cgggcccacc cgcaagcatt accagcccta tgccccacca     180
cgcgacttcg cagcctatcg ctcc                                             204

<210> SEQ ID NO 14
<211> LENGTH: 282
<212> TYPE: DNA
<213> ORGANISM: Artificial Sequence
<220> FEATURE:
<223> OTHER INFORMATION: IL2 receptor zeta] chain signaling domain

<400> SEQUENCE: 14
aactgcagga acaccgggcc atggctgaag aaggtcctga agtgtaacac cccagacccc      60
tcgaagttct ttcccagct gagctcagag catggaggag acgtccagaa gtggctctct     120
tcgcccttcc cctcatcgtc cttcagccct ggcggcctgg cacctgagat tcgccacta     180 gaagtgctgg agagggacaa ggtgacgcag ctgctccccc tgaacactga tgcctacttg     240

-continued

| tccctccaag aactccaggg tcaggaccca actcacttgg tg | 282 |

<210> SEQ ID NO 15
<211> LENGTH: 339
<212> TYPE: DNA
<213> ORGANISM: Artificial Sequence
<220> FEATURE:
<223> OTHER INFORMATION: CD3 zeta signaling domain

<400> SEQUENCE: 15

| agagtgaagt tcagcaggag cgcagacgcc ccgcgtacc agcagggcca gaaccagctc | 60 |
| tataacgagc tcaatctagg acgaagagag gagtacgatg ttttggacaa gagacgtggc | 120 |
| cgggaccctg agatgggggg aaagccgcag agaaggaaga accctcagga aggcctgtac | 180 |
| aatgaactgc agaaagataa gatggcggag gcctacagtg agattgggat gaaaggcgag | 240 |
| cgccggaggg gcaaggggca cgatggcctt taccagggtc tcagtacagc caccaaggac | 300 |
| acctacgacg cctatcgcca ccaggccctg ccccttaa | 339 |

<210> SEQ ID NO 16
<211> LENGTH: 63
<212> TYPE: DNA
<213> ORGANISM: Artificial Sequence
<220> FEATURE:
<223> OTHER INFORMATION: signal peptide coding fragment

<400> SEQUENCE: 16

| atggccctcc ctgtcaccgc cctgctgctt ccgctggctc ttctgctcca cgccgctcgg | 60 |
| ccc | 63 |

<210> SEQ ID NO 17
<211> LENGTH: 135
<212> TYPE: DNA
<213> ORGANISM: Artificial Sequence
<220> FEATURE:
<223> OTHER INFORMATION: CD8 hinge region coding fragment

<400> SEQUENCE: 17

| accacgacgc cagcgccgcg accaccaaca ccggcgccca ccatcgcgtc gcagcccctg | 60 |
| tccctgcgcc cagaggcgtg ccggccagcg gcggggggcg cagtgcacac gagggggctg | 120 |
| gacttcgcct gtgat | 135 |

<210> SEQ ID NO 18
<211> LENGTH: 1335
<212> TYPE: DNA
<213> ORGANISM: Artificial Sequence
<220> FEATURE:
<223> OTHER INFORMATION: promoter

<400> SEQUENCE: 18

| gagtaattca tacaaaagga ctcgcccctg ccttggggaa tcccagggac cgtcgttaaa | 60 |
| ctcccactaa cgtagaaccc agagatcgct gcgttccgc cccctcaccc gcccgctctc | 120 |
| gtcatcactg aggtggagaa gagcatgcgt gaggctccgg tgcccgtcag tgggcagagc | 180 |
| gcacatcgcc cacagtcccc gagaagttgg ggggaggggt cggcaattga accggtgcct | 240 |
| agagaaggtg gcgcggggta aactgggaaa gtgatgtcgt gtactggctc cgcctttttc | 300 |
| ccgagggtgg gggagaaccg tatataagtg cagtagtcgc cgtgaacgtt ctttttcgca | 360 |
| acgggtttgc cgccagaaca caggtaagtg ccgtgtgtgg ttcccgcggg cctggcctct | 420 |
| ttacgggtta tggcccttgc gtgccttgaa ttacttccac gcccctggct gcagtacgtg | 480 |

```
attcttgatc ccgagcttcg ggttggaagt gggtgggaga gttcgaggcc ttgcgcttaa    540
ggagcccctt cgcctcgtgc ttgagttgag gcctggcttg ggcgctgggg ccgccgcgtg    600
cgaatctggt ggcaccttcg cgcctgtctc gctgctttcg ataagtctct agccatttaa    660
aatttttgat gacctgctgc gacgcttttt ttctggcaag atagtcttgt aaatgcgggc    720
caagatctgc acactggtat ttcggttttt ggggccgcgg gcggcgacgg ggcccgtgcg    780
tcccagcgca catgttcggc gaggcggggc ctgcgagcgc ggccaccgag aatcggacgg    840
gggtagtctc aagctggccg gcctgctctg gtgcctggcc tcgcgccgcc gtgtatcgcc    900
ccgccctggg cggcaaggct ggcccggtcg gcaccagttg cgtgagcgga aagatggccg    960
cttcccggcc ctgctgcagg gagctcaaaa tggaggacgc ggcgctcggg agagcgggcg   1020
ggtgagtcac ccacacaaag gaaaagggcc tttccgtcct cagccgtcgc ttcatgtgac   1080
tccacggagt accgggcgcc gtccaggcac ctcgattagt tctcgagctt ttggagtacg   1140
tcgtctttag gttgggggga ggggttttat gcgatggagt ttccccacac tgagtgggtg   1200
gagactgaag ttaggccagc ttggcacttg atgtaattct ccttggaatt tgcccttttt   1260
gagtttggat cttggttcat tctcaagcct cagacagtgg ttcaaagttt ttttcttcca   1320
tttcaggtgt cgtga                                                   1335
```

HLA-G SPECIFIC CHIMERIC ANTIGEN RECEPTOR, NUCLEIC ACID, HLA-G SPECIFIC CHIMERIC ANTIGEN RECEPTOR EXPRESSION PLASMID, HLA-G SPECIFIC CHIMERIC ANTIGEN RECEPTOR EXPRESSING CELL, USE THEREOF, AND PHARMACEUTICAL COMPOSITION FOR TREATING CANCER

RELATED APPLICATIONS

This application claims priority to Taiwan Application Serial Number 108138478, filed Oct. 24, 2019, which is herein incorporated by reference.

SEQUENCE LISTING

The sequence listing submitted via EFS, in compliance with 37 CFR § 1.52(e)(5), is incorporated herein by reference. The sequence listing text file submitted via EFS contains the file "CP-4595-US_SEQ_LIST", created on Jun. 1, 2020, which is 12,342 bytes in size.

BACKGROUND

Technical Field

The present disclosure relates to a pharmaceutical product containing an antigen or an antibody. More particularly, the present disclosure relates to a chimeric antigen receptor, a nucleic acid encoding the chimeric antigen receptor, a chimeric antigen receptor expression plasmid, a chimeric antigen receptor expressing cell, a pharmaceutical composition for treating cancer, and use of the chimeric antigen receptor expressing cell.

Description of Related Art

Cancer, also known as malignancy, is a state of abnormal proliferation of cells, and these proliferating cells may invade other parts of the body as a disease caused by a malfunction in the control of cell division and proliferation. The number of people suffering from cancer worldwide has a growing trend. Cancer is one of the top ten causes of death for the Chinese people and has been the top ten causes of death for twenty-seven consecutive years.

Conventional cancer treatments include surgery, radiation therapy, chemotherapy, and target therapy. Cancer immunotherapy is another method for treating cancer except the above methods. The immune system of the patient is activated in the cancer immunotherapy by using tumor cells or tumor antigens to induce specific cellular and humoral immune responses for enhancing the anti-cancer ability of the patient, preventing the growth, spread, and recurrence of tumors, and achieving the purpose of removing or controlling tumors.

There are three main directions for the cancer immunotherapy: the tumor vaccine, the cell therapy and the immune checkpoint inhibitor. The chimeric antigen receptor immune cell technology is one of the cell therapy developing very rapidly in recent years. In conventional technology, the chimeric antigen receptor immune cell transfecting a chimeric protein, which couples the antigen binding portion having capable of recognizing a certain tumor antigen of the antibody to the intracellular portion of the CD3-δ chain or FcεRIγ in vitro, into the immune cell by a transduction method to express the chimeric antigen receptor. The chimeric antigen receptor immune cell technology has a significant therapeutic effect in the treatment of acute leukemia and non-Hodgkin's lymphoma, and it is considered to be one of the most promising treatments for cancer. However, the cell therapy of the chimeric antigen receptor immune cell currently has the following disadvantages: lack of unique tumor-associated antigens, low efficiency of homing of immune cells to tumor sites, and inability to overcome the immunosuppressive microenvironment of solid tumors. Accordingly, the efficacy of the chimeric antigen receptor immune cell in solid tumors is greatly limited.

SUMMARY

According to one aspect of the present disclosure, a HLA-G specific chimeric antigen receptor includes, in order from an N-terminus to a C-terminus, an antigen recognition domain, a transmembrane domain, an IL2 receptor β chain signaling domain, and a CD3ζ signaling domain. The antigen recognition domain includes a monoclonal antibody fragment specific to human leukocyte antigen G (HLA-G) and includes an amino acid sequence of SEQ ID NO: 1. The transmembrane domain includes an amino acid sequence of SEQ ID NO: 2. The IL2 receptor β chain signaling domain includes an amino acid sequence of SEQ ID NO: 3. The CD3ζ signaling domain includes an amino acid sequence of SEQ ID NO: 4.

According to another aspect of the present disclosure, a nucleic acid encoding the HLA-G specific chimeric antigen receptor according to the aforementioned aspect includes, in order from a 5' end to a 3' end, an antigen recognition domain coding fragment including a nucleic acid sequence of SEQ ID NO: 12, a transmembrane domain coding fragment including a nucleic acid sequence of SEQ ID NO: 13, an IL2 receptor β chain signaling domain coding fragment including a nucleic acid sequence of SEQ ID NO: 14, and a CD3 signaling domain coding fragment including a nucleic acid sequence of SEQ ID NO: 15.

According to still another aspect of the present disclosure, a HLA-G specific chimeric antigen receptor expression plasmid includes, in order from a 5' end to a 3' end, a promoter including a nucleic acid sequence of SEQ ID NO: 18 and the nucleic acid according to the foregoing aspect.

According to yet another aspect of the present disclosure, a HLA-G specific chimeric antigen receptor expressing cell includes an immune cell and the chimeric antigen receptor expression plasmid according to the foregoing aspect.

According to further another aspect of the present disclosure, pharmaceutical composition for treating a cancer includes the HLA-G specific chimeric antigen receptor expressing cell according to the foregoing aspect and a pharmaceutically acceptable carrier.

According to still another aspect of the present disclosure, a method for inhibiting a proliferation of a tumor cell includes administering a composition containing a plurality of the HLA-G specific chimeric antigen receptor expressing cells according to the foregoing aspect to a subject in need for a treatment of a tumor.

BRIEF DESCRIPTION OF THE DRAWINGS

The present disclosure can be more fully understood by reading the following detailed description of the embodiment, with reference made to the accompanying drawings as follows.

DETAILED DESCRIPTION

A HLA-G specific chimeric antigen receptor, a nucleic acid encoding the HLA-G specific chimeric antigen receptor, a HLA-G specific chimeric antigen receptor expression plasmid including the nucleic acid, a HLA-G specific chimeric antigen receptor expressing cell including the HLA-G specific chimeric antigen receptor expression plasmid, a use thereof, and a pharmaceutical composition for treating cancer including the HLA-G specific chimeric antigen receptor expressing cell are provided. A tumor cell specific binding ability of the HLA-G specific chimeric antigen receptor of the present disclosure, especially a specific binding ability to human leukocyte antigen G (HLA-G) expressed on the plasma membrane of tumor cells, is confirmed by in vitro cell assay of the tumor cells. Accordingly, the HLA-G specific chimeric antigen receptor expressing cell of the present disclosure, which expresses the HLA-G specific chimeric antigen receptor of the present disclosure, can specifically target the tumor cells to avoid the off-target effect, thereby effectively killing the tumor cells. Therefore, the HLA-G specific chimeric antigen receptor expressing cell can be used for inhibiting the proliferation of the tumor cells in a subject in need for a treatment of a tumor. The pharmaceutical composition for treating cancer of the present disclosure includes the HLA-G specific chimeric antigen receptor expressing cell of the present disclosure, and can further include a chemotherapy drug, which can effectively kill tumor cells and thereby treat cancer.

The term "human leukocyte antigen G (HLA-G)" is a protein that in humans is encoded by the HLA-G gene. The HLA-G belongs to nonclassical class I major histocompatibility complex (MHC) with a heavy chain of approximately 45 kDa. HLA-G is expressed on fetal derived placental cells, and is active in the negative regulation of immune response. HLA-G may play a role in immune tolerance in pregnancy.

Reference will now be made in detail to the present embodiments of the present disclosure, examples of which are illustrated in the accompanying drawings.

Figure 1:
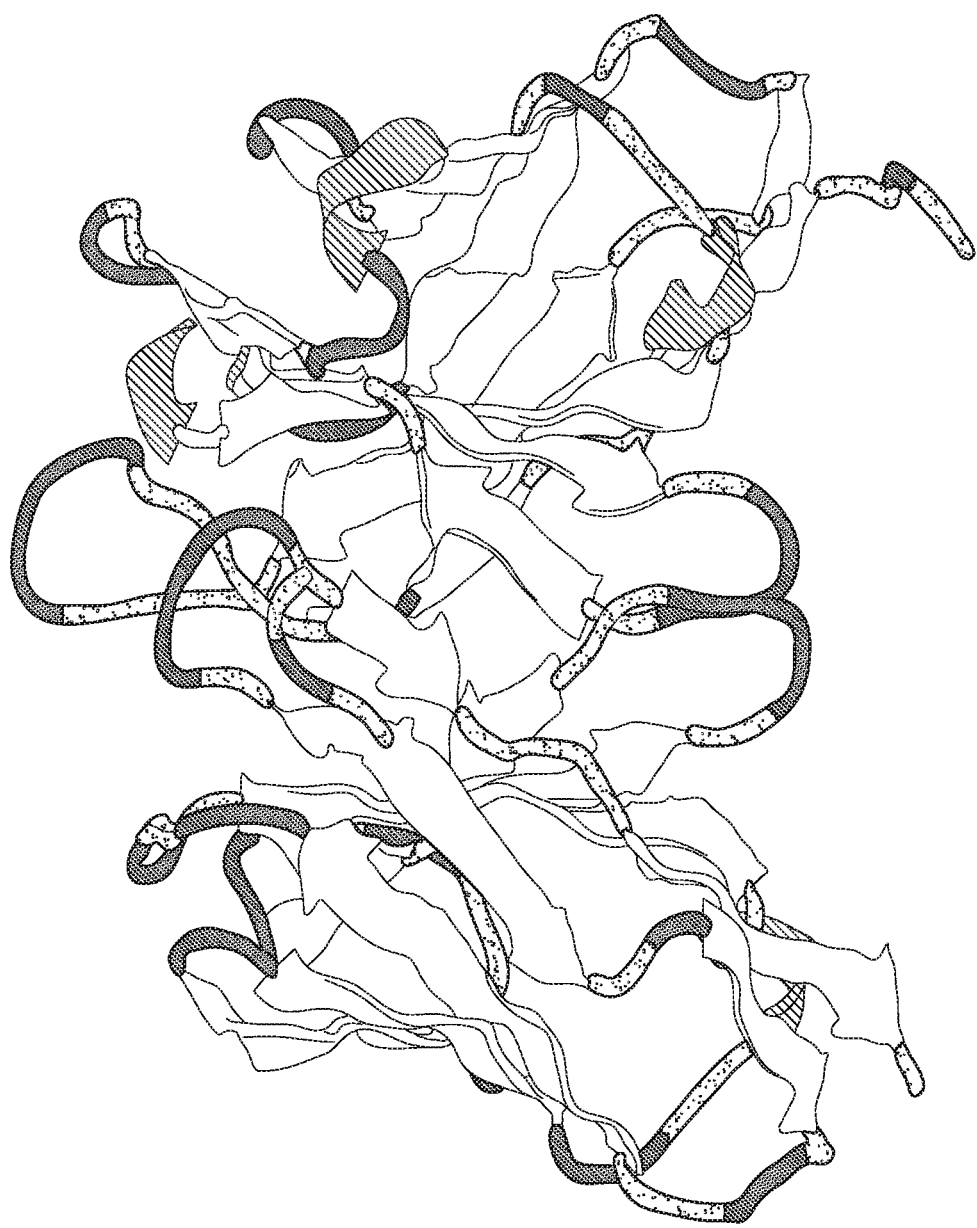
FIG. 1 is a schematic view showing a protein structure of an antigen recognition domain according to one embodiment of the present disclosure.

I. HLA-G Specific Chimeric Antigen Receptor, Nucleic Acid and HLA-G Specific Chimeric Antigen Receptor Expression Plasmid of the Present Disclosure The HLA-G specific chimeric antigen receptor of the present disclosure includes, in order from an N-terminus to a C-terminus, an antigen recognition domain including an amino acid sequence of SEQ ID NO: 1, a transmembrane domain including an amino acid sequence of SEQ ID NO: 2, an IL2 receptor β chain signaling domain including an amino acid sequence of SEQ ID NO: 3, and a CD3ζ signaling domain including an amino acid sequence of SEQ ID NO: 4. The antigen recognition domain includes a monoclonal antibody fragment specific to human leukocyte antigen G (HLA-G). Preferably, a signal peptide including an amino acid sequence of SEQ ID NO: 5 can be linked to the N-terminus of the antigen recognition domain, and a CD8 hinge region including an amino acid sequence of SEQ ID NO: 11 can link the antigen recognition domain and the transmembrane domain. In detail, the antigen recognition domain including the amino acid sequence of SEQ ID NO: 1 includes a heavy chain (HC) immunoglobulin variable domain sequence and a light chain (LC) immunoglobulin variable domain sequence. The HC immunoglobulin variable domain sequence includes a CDRH1 including an amino acid sequence of SEQ ID NO: 6, a CDRH2 including an amino acid sequence of SEQ ID NO: 7, and a CDRH3 including an amino acid sequence of SEQ ID NO: 8. The LC immunoglobulin variable domain sequence includes a CDRL1 including an amino acid sequence of SEQ ID NO: 9, a CDRL2 including an amino acid sequence of RMS, and a CDRL3 including an amino acid sequence of SEQ ID NO: 10. Please refer to FIG. 1, which is a schematic view showing a protein structure of the antigen recognition domain according to one embodiment of the present disclosure. The looped region in which the sprinkle is indicated represents the variable domain in the antigen recognition domain of the present disclosure.

The nucleic acid of the present disclosure encoding the HLA-G specific chimeric antigen receptor of the present disclosure includes, in order from a 5' end to a 3' end, an antigen recognition domain coding fragment including a nucleic acid sequence of SEQ ID NO: 12, a transmembrane domain coding fragment including a nucleic acid sequence of SEQ ID NO: 13, an IL2 receptor β chain signaling domain coding fragment including a nucleic acid sequence of SEQ ID NO: 14, and a CD3ζ signaling domain coding fragment including a nucleic acid sequence of SEQ ID NO: 15. Preferably, a signal peptide coding fragment including a nucleic acid sequence of SEQ ID NO: 16 can be linked to the 5' end of the antigen recognition domain coding fragment, and a CD8 hinge region coding fragment including a nucleic acid sequence of SEQ ID NO: 17 can link the antigen recognition domain coding fragment and the transmembrane domain coding fragment. The antigen recognition domain coding fragment including the nucleic acid sequence of SEQ ID NO: 12 encodes the antigen recognition domain including the amino acid sequence of SEQ ID NO: 1. The transmembrane domain coding fragment including the nucleic acid sequence of SEQ ID NO: 13 encodes the transmembrane domain including the amino acid sequence of SEQ ID NO: 2. The IL2 receptor β chain signaling domain coding fragment including the nucleic acid sequence of SEQ ID NO: 14 encodes the IL2 receptor β chain signaling domain including the amino acid sequence of SEQ ID NO: 3. The CD3ζ signaling domain coding fragment including the nucleic acid sequence of SEQ ID NO: 15 encodes the CD3ζ signaling domain including the amino acid sequence of SEQ ID NO: 4. The signal peptide coding fragment including the nucleic acid sequence of SEQ ID NO: 16 encodes the signal peptide including the amino acid sequence of SEQ ID NO: 5. The CD8 hinge region coding fragment including the nucleic acid sequence of SEQ ID NO: 17 encodes the CD8 hinge region including the amino acid sequence of SEQ ID NO: 11.

Figure 2:
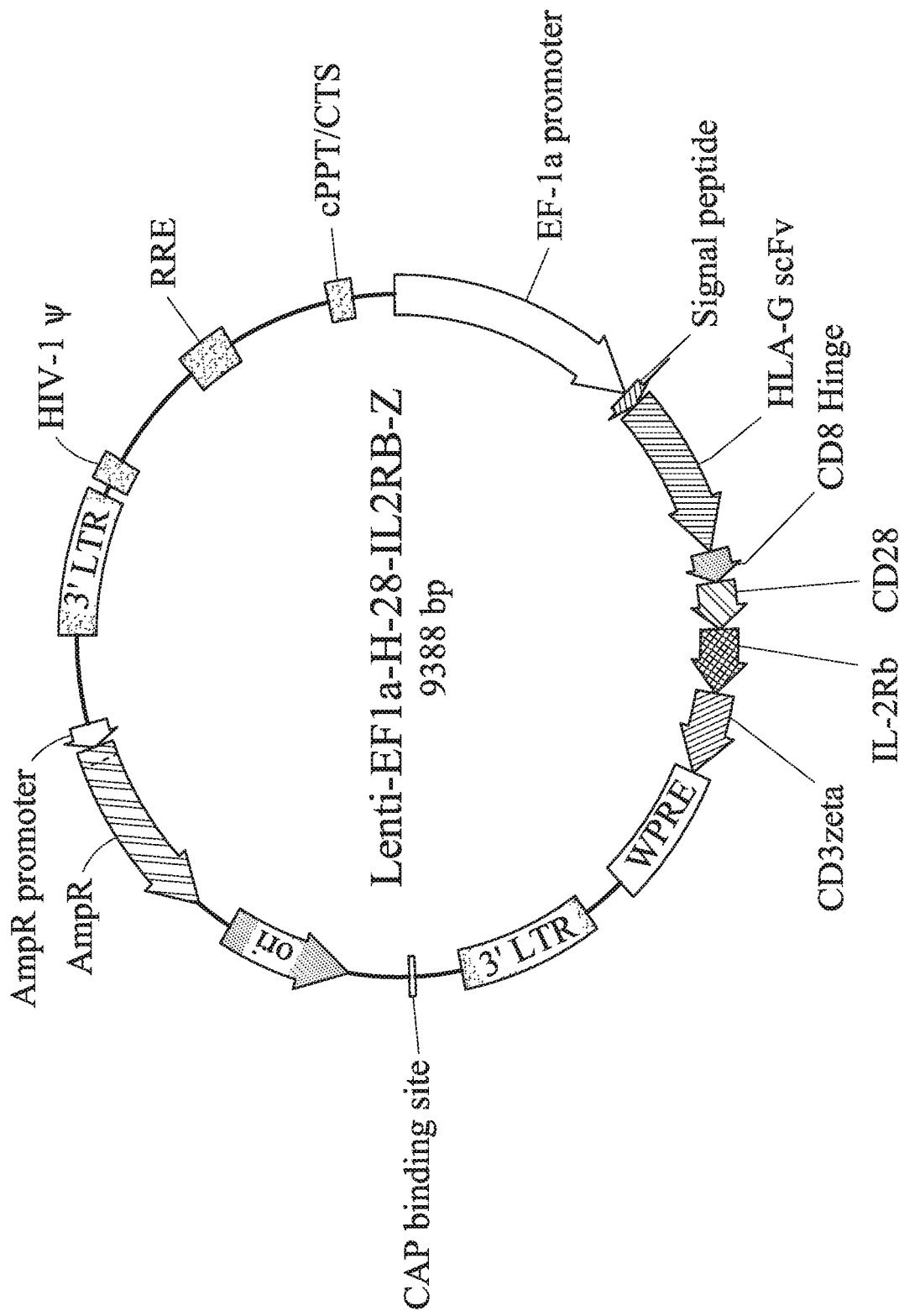
FIG. 2 is a schematic view showing a construction of a HLA-G specific chimeric antigen receptor expression plasmid according to another embodiment of the present disclosure.

FIG. 2 is a schematic view showing a construction of a HLA-G specific chimeric antigen receptor expression plasmid according to another embodiment of the present disclosure. In detail, according to one example of this embodiment, the HLA-G specific chimeric antigen receptor expression plasmid is Lenti-EF1a-H-28-IL2RB-Z plasmid, wherein the insert thereof includes a promoter, an antigen recognition domain coding fragment, a transmembrane domain coding fragment, a IL2 receptor β chain signaling domain coding fragment and a CD3ζ signaling domain coding fragment. The promoter is the EF-1 alpha promoter including a nucleic acid sequence of SEQ ID NO: 18. The antigen recognition domain coding fragment includes the nucleic acid sequence of SEQ ID NO: 12. The transmembrane domain coding fragment includes the nucleic acid sequence of SEQ ID NO: 13. The IL2 receptor β chain signaling domain coding fragment includes the nucleic acid sequence of SEQ ID NO: 14. The CD3ζ signaling domain coding fragment includes the nucleic acid sequence of SEQ ID NO: 15. In addition, the insert of the Lenti-EF1a-H-28-IL2RB-Z plasmid further includes a signal peptide coding fragment including a nucleic acid sequence of SEQ ID NO: 16, and the CD8 hinge region coding fragment including the nucleic acid sequence of SEQ ID NO: 17. The signal peptide coding fragment is linked to the 5' end of the antigen recognition domain coding fragment, and the CD8 hinge region coding fragment links the antigen recognition domain coding fragment and the transmembrane domain coding fragment. Then, the insert is constructed on Creative Biolabs vector (Creative Biolabs, NY, USA) to obtain the Lenti-EF1a-H-28-IL2RB-Z plasmid. The Creative Biolabs vector is a lentivirus vector system, so that the constructed HLA-G specific chimeric antigen receptor expression plasmid can be transfected into expression cells to produce lentiviruses, and the HLA-G specific chimeric antigen receptor can be subsequently transduced into the immune cells using lentiviruses.

II. HLA-G Specific Chimeric Antigen Receptor Expressing Cell, Use Thereof and Pharmaceutical Composition for Treating Cancer of the Present Disclosure The HLA-G specific chimeric antigen receptor expressing cell of the present disclosure is obtained by transducing the HLA-G specific chimeric antigen receptor of the present disclosure into the immune cell using lentiviruses. Preferably, the immune cell can be a T lymphocyte or a natural killer (NK) cell. More preferably, the NK cell can be a NK-92 cell line or a primary NK cell. In detail, the constructed Lenti-EF1a-H-28-IL2RB-Z plasmid is transfected into a 293T cell line using lipofectamine 3000 (Invitrogen) to prepare the lentiviruses carrying the HLA-G specific chimeric antigen receptor of the present disclosure. For obtaining one example of the HLA-G specific chimeric antigen receptor expressing cell, the supernatant containing the prepared lentiviruses and OPTI-MEM® (Invitrogen) containing 8 μg/ml of polybrene (Sigma-Aldrich) are used to culture the primary T lymphocytes for 3 days to transduce the HLA-G specific chimeric antigen receptor of the present disclosure into the primary T lymphocytes. For obtaining another example of the HLA-G specific chimeric antigen receptor expressing cell, the supernatant containing the prepared lentiviruses and the OPTI-MEM® (Invitrogen) containing 50 μg/ml of protamine sulfate (Sigma-Aldrich) are used to culture the primary NK cells for 7 days to transduce the HLA-G specific chimeric antigen receptor of the present disclosure into the primary NK cell. The obtained HLA-G specific chimeric antigen receptor expressing cell has an effect of inducing tumor cell death in mammals, so that the HLA-G specific chimeric antigen receptor expressing cell can be used for inhibiting a proliferation of tumor cells in a subject in need for a treatment of a tumor. Preferably, the tumor cell can be a breast cancer cell, a glioblastoma multiforme cell, a pancreatic cancer cell or an ovarian cancer cell.

The pharmaceutical composition for treating a cancer of the present disclosure includes the HLA-G specific chimeric antigen receptor expressing cell of the present disclosure and a pharmaceutically acceptable carrier. Preferably, the pharmaceutical composition for treating cancer can further include a chemotherapy drug. More preferably, the chemotherapy drug can be doxorubicin (Dox), temozolomide (TMZ), gemcitabine (Gem) or carboplatin (CB).

The HLA-G specific chimeric antigen receptor expressing cell and the pharmaceutical composition for treating the cancer will be further described by the following embodiments. In the following, an Example 1 and an Example 2 will be further provided to illustrate the accompanied efficacies of the HLA-G specific chimeric antigen receptor expressing cell and the pharmaceutical composition for treating the cancer on inducing tumor cell death. However, the present disclosure is not limited thereto. The tumor cells used are human breast cancer cell line MDA-MB-231, human malignant brain tumor cell line DBTRG-05MG (hereinafter referred to as DBTRG), human pancreatic cancer cell line AsPC1, and human ovarian cancer cell line SKOV3. The tumor cell lines used are all purchased from the American Type Culture Collection (ATCC). The human breast cancer cell line MDA-MB-231 is a triple-negative breast cancer cell line, that is, the hormone receptor (ER, PR) and HER-2 receptor thereof are negative, and the human breast cancer cell line MDA-MB-231 is cultured in RPMI culture medium containing 10% fetal bovine serum (FBS). The human malignant brain tumor cell line DBTRG is cultured in DMEM culture medium containing 10% FBS. The human pancreatic cancer cell line AsPC1 is cultured in RPMI culture medium containing 10% FBS. The human ovarian cancer cell line SKOV3 is cultured in McCoy's 5A culture medium containing 10% FBS.

EXAMPLES 2.1. Example 1

The HLA-G specific chimeric antigen receptor of the present disclosure is transduced into the primary NK cell to obtain the HLA-G specific chimeric antigen receptor expressing cell of Example 1 of the present disclosure (hereinafter referred to as Example 1). The effects of the Example 1 and the pharmaceutical composition for treating cancer including the Example 1 of the present disclosure on inducing the death of the breast cancer cells, the glioblastoma multiforme cells, the pancreatic cancer cells, and the ovarian cancer cells are further demonstrated in following experiments.

First, the human breast cancer cell line MDA-MB-231, the human malignant brain tumor cell line DBTRG, the human pancreatic cancer cell line AsPC1 and the human ovarian cancer cell line SKOV3 are seeded in a 12-well plate at a density of $1 \times 10^5$ cells/well. The cells are subsequently incubated for 24 hours. Each type of the tumor cells is divided into six groups. In a control, the tumor cells are untreated. In a group 1, the tumor cells are treated with the chemotherapy drug. In a group 2, the tumor cells are treated with the parental primary NK cell. In a group 3, the tumor cells are treated with the parental primary NK cell and the chemotherapy drug. In the groups 2 and 3, the number of the parental primary NK cell treated is $1\times10^5$ cells. In a group 4, the tumor cells are treated with the Example 1. In a group 5, the tumor cells are treated with the Example 1 and the chemotherapy drug. In the groups 4 and 5, the number of the Example 1 treated is $1\times10^5$ cells. The chemotherapy drug used for treating the human breast cancer cell line MDA-MB-231 is doxorubicin (200 nM), the chemotherapy drug used for treating the human malignant brain tumor cell line DBTRG is temozolomide (80 μg/mL), the chemotherapy drug used for treating the human pancreatic cancer cell line AsPC1 is gemcitabine (20 μM), and the chemotherapy drug used for treating the human ovarian cancer cell line SKOV3 is carboplatin (20 μM). The treated cells are stained with Annexin V-FITC and propidium iodide (PI), and the apoptosis and the death of the tumor cells are detected by the flow cytometry. The sum of the percentage of cells stained with Annexin V-FITC and/or PI (that is the percentage of cells in the first quadrant, the second quadrant, and the fourth quadrant of the bivariate flow cytometry scatter plot) are calculated to obtain the cytotoxicity. The results of the cytotoxicity are counted after the three independent trials in each group.

Figure 3A:
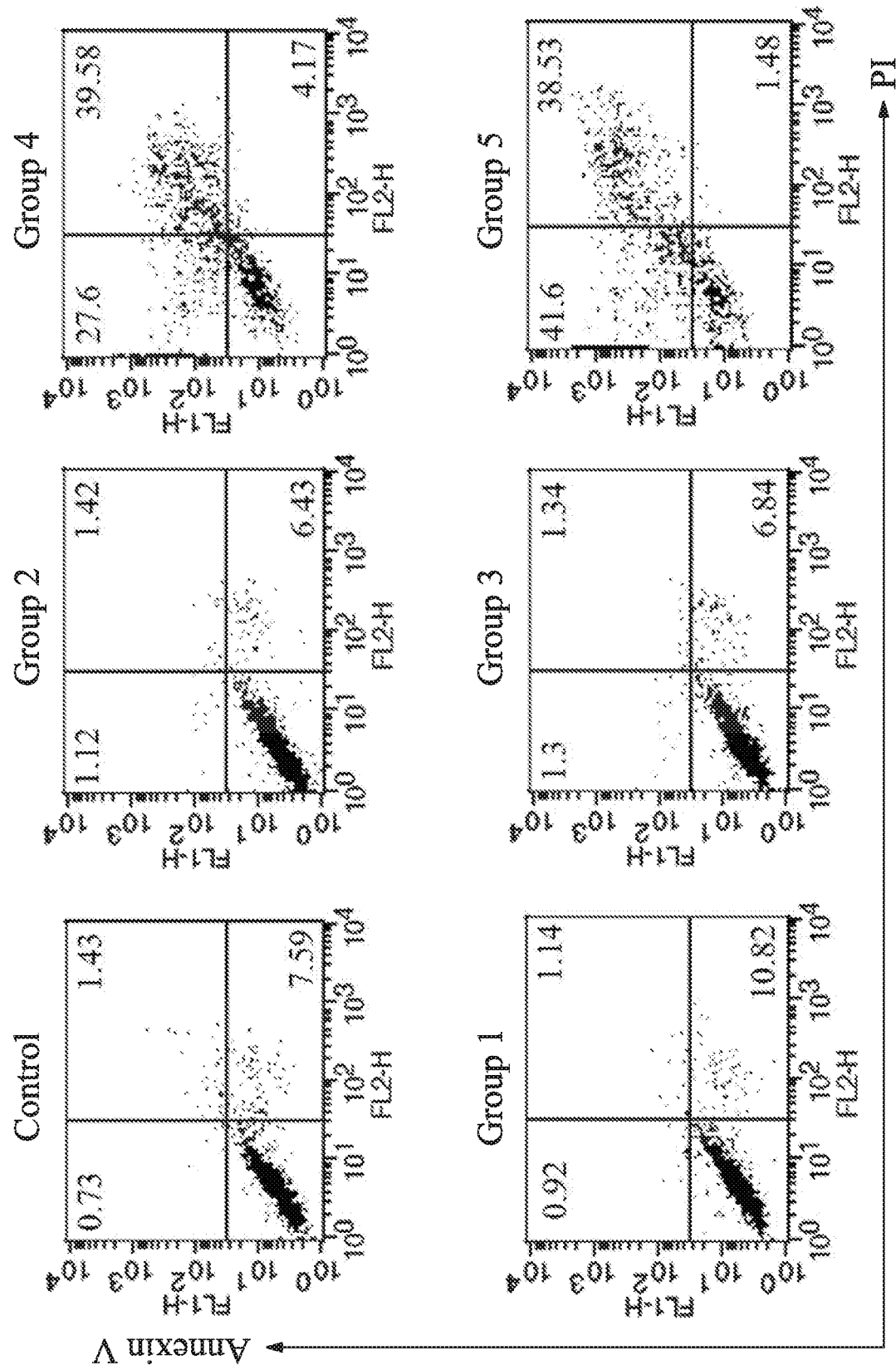
FIGS. 3A, 3B, 3C, 3D, 3E, 3F, 3G and 3H show analytical results of tumor cell death induced by HLA-G specific chimeric antigen receptor expressing cells according to Example 1 of the present disclosure.
Figure 3B:
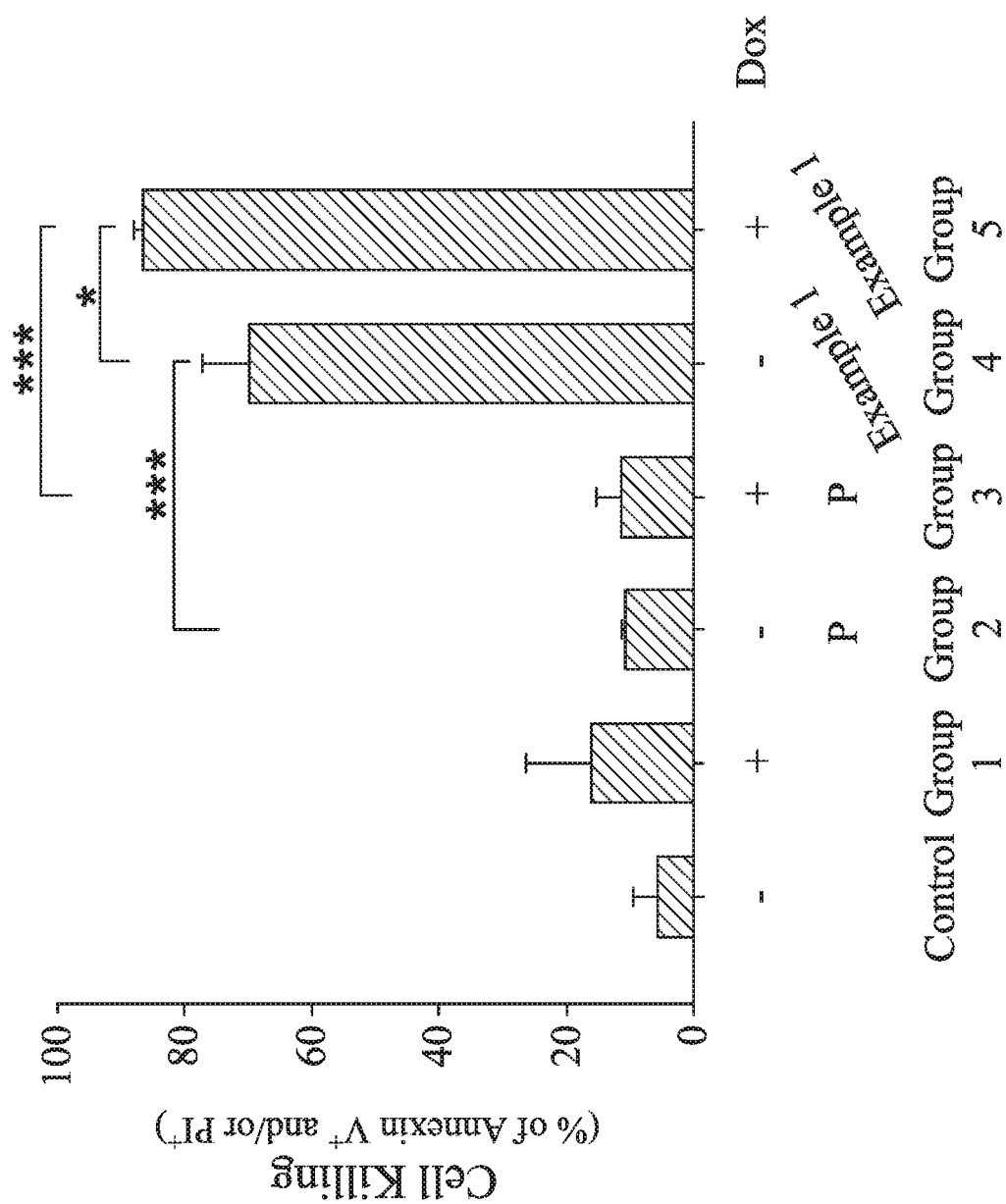
Figure 3C:
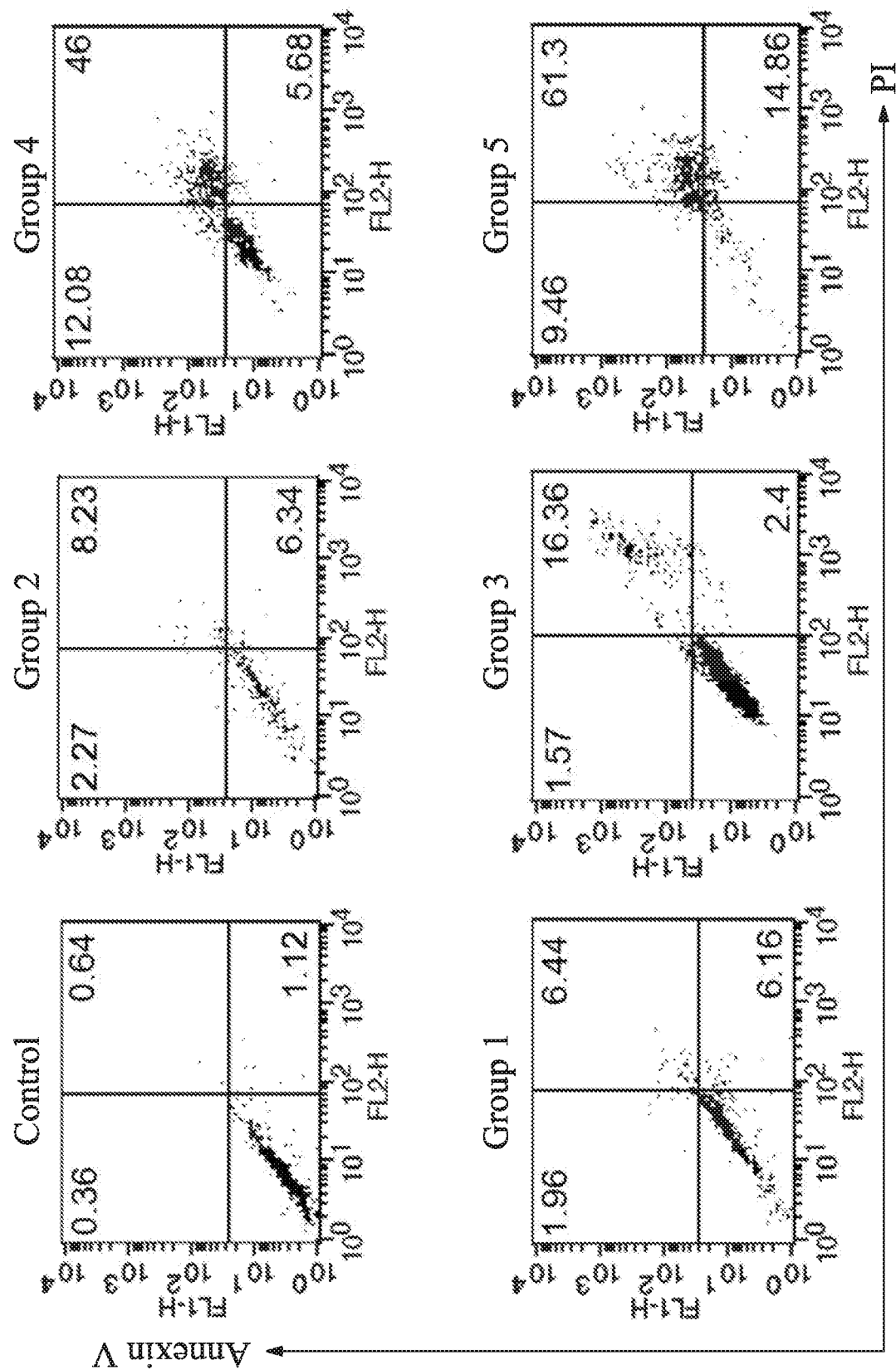
Figure 3D:
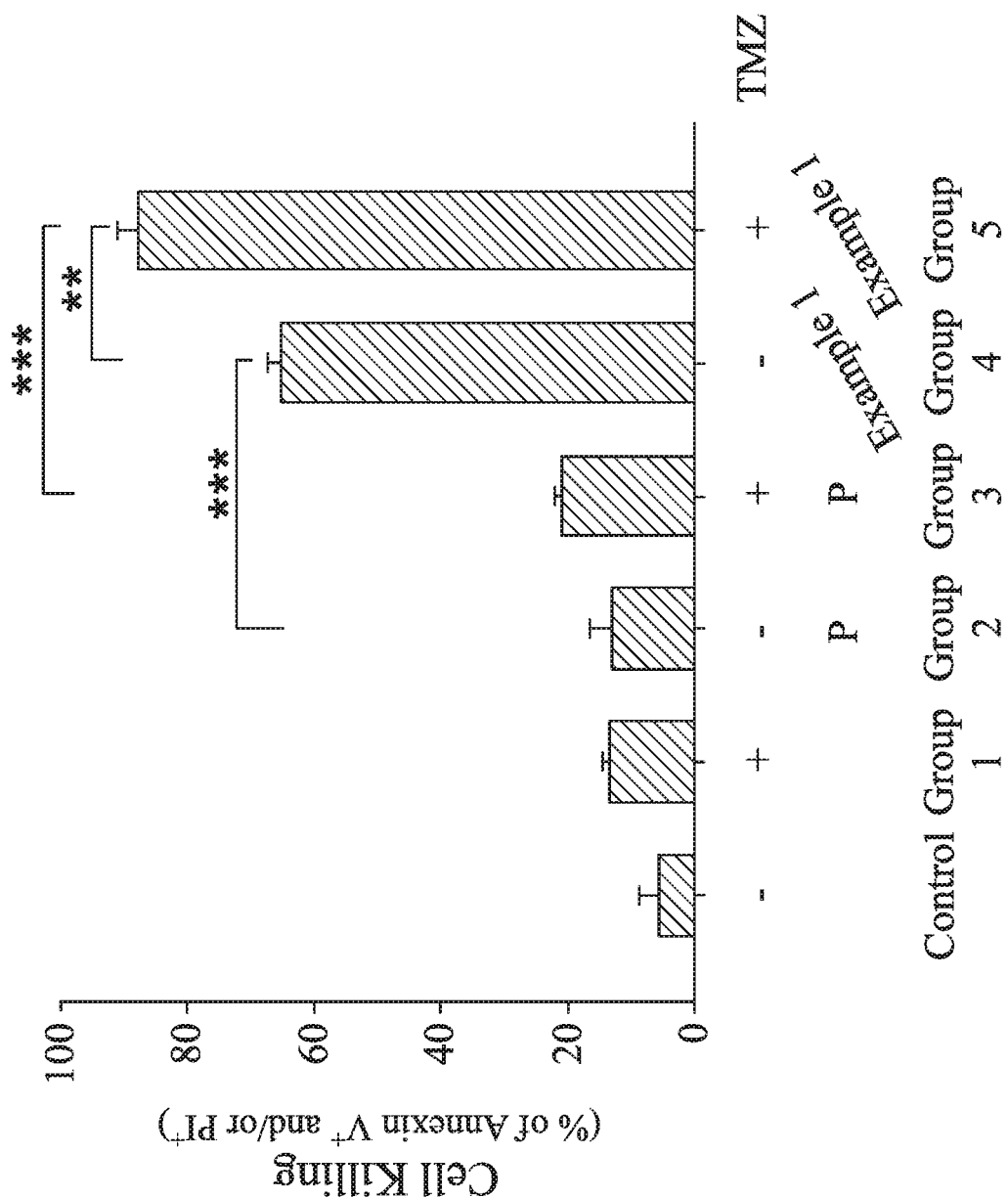
Figure 3E:
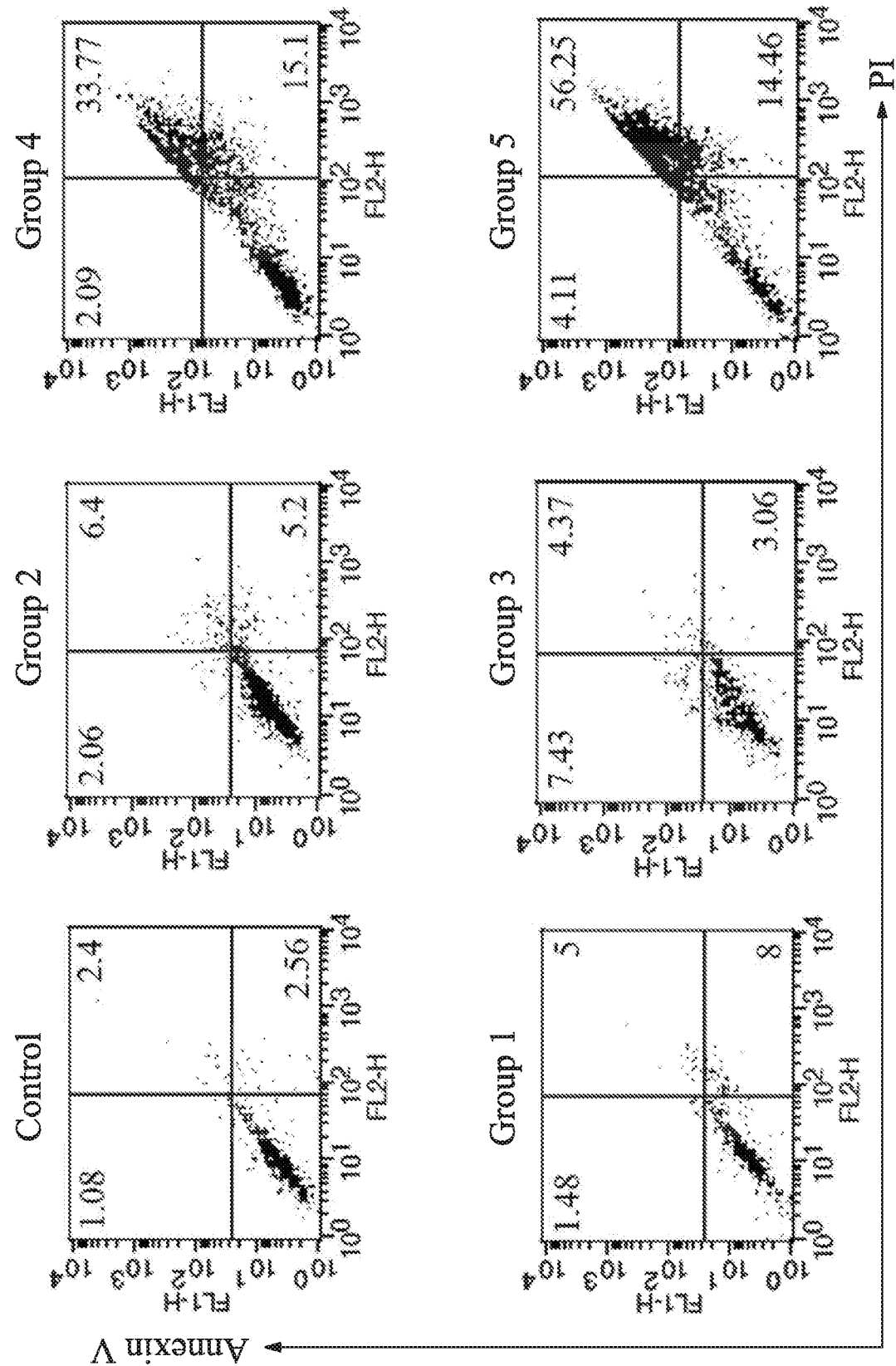
Figure 3F:
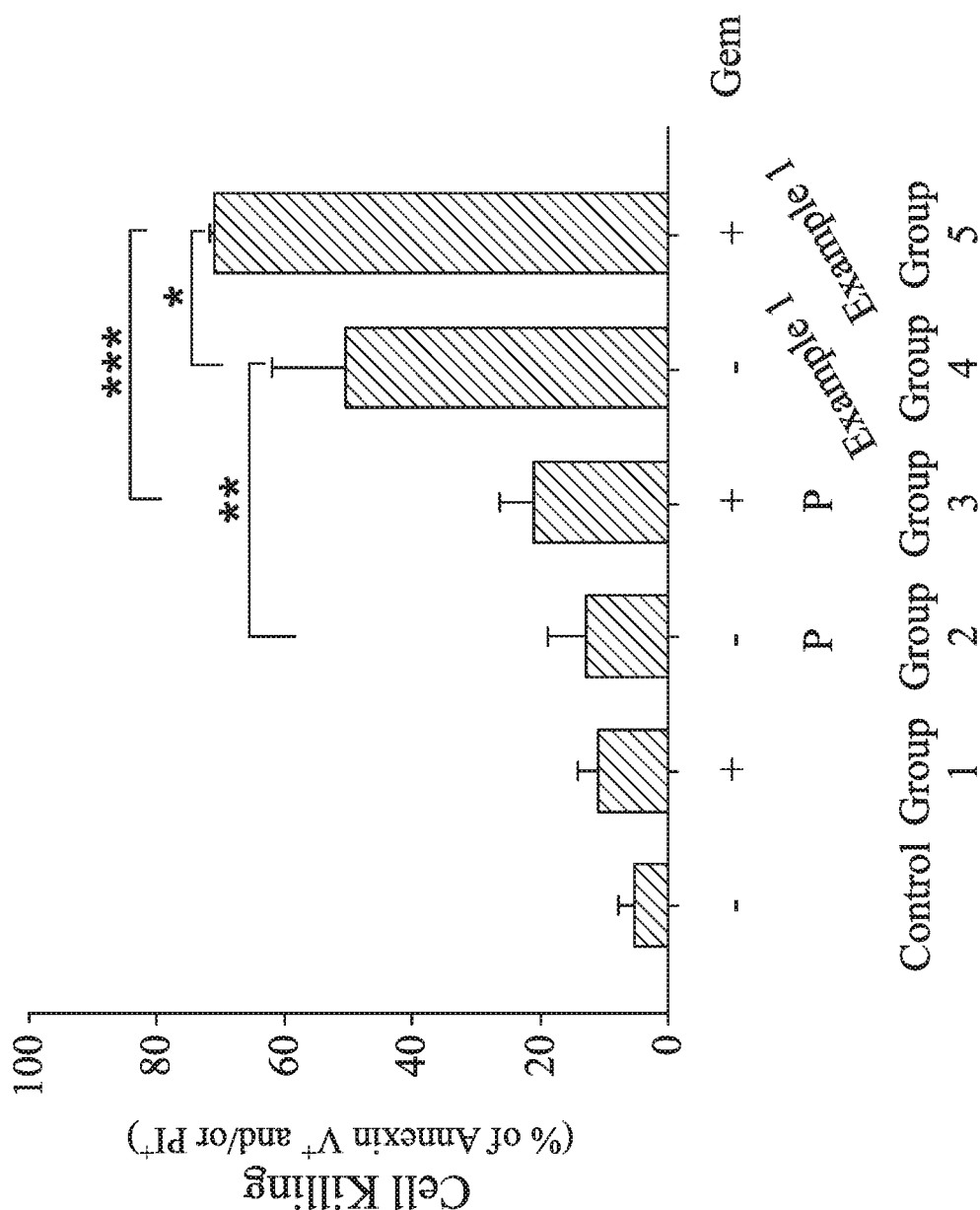
Figure 3G:
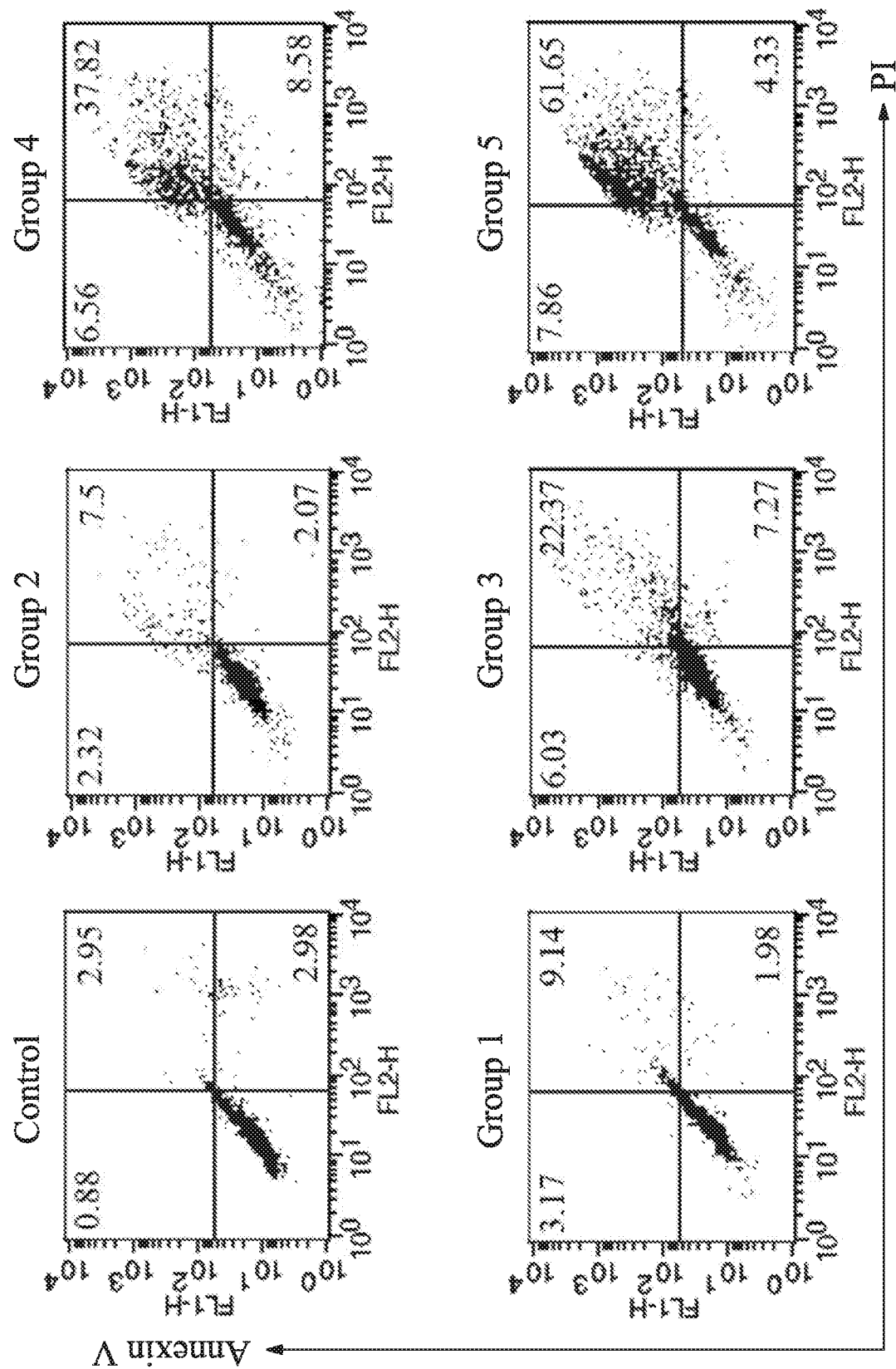
Figure 3H:
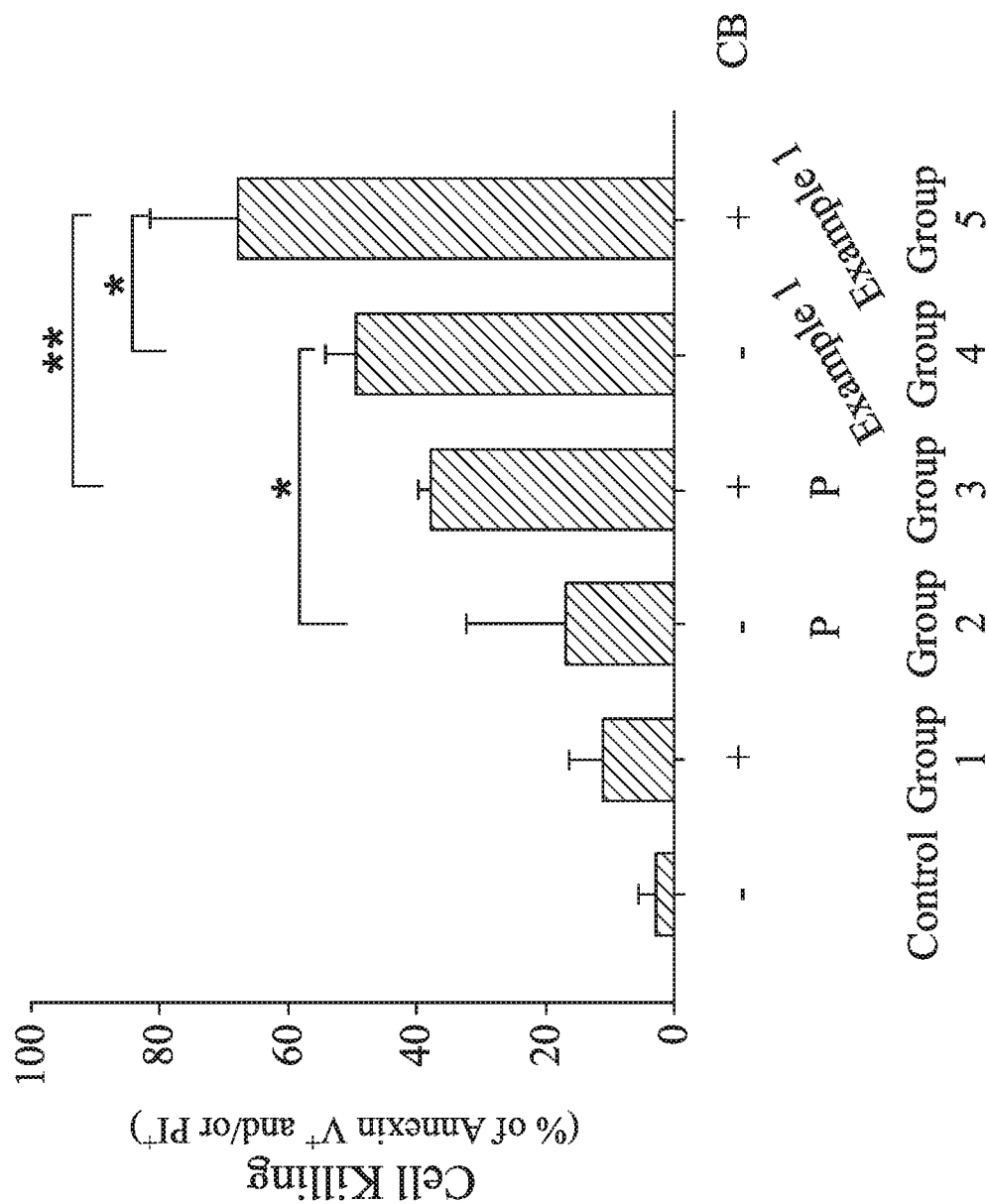

Please refer to FIGS. 3A, 3B, 3C, 3D, 3E, 3F, 3G and 3H, which show analytical results of tumor cell death induced by the Example 1. FIG. 3A is a graph showing the analytical results of the death of the human breast cancer cell line MDA-MB-231 induced by the Example 1, and FIG. 3B is a statistical chart of FIG. 3A after the three independent trials. FIG. 3C is a graph showing the analytical results of the death of the human malignant brain tumor cell line DBTRG induced by the Example 1, and FIG. 3D is a statistical chart of FIG. 3C after the three independent trials. FIG. 3E is a graph showing the analytical results of the death of the human pancreatic cancer cell line AsPC1 induced by the Example 1, and FIG. 3F is a statistical chart of FIG. 3E after the three independent trials. FIG. 3G is a graph showing the analytical results of the death of the human ovarian cancer cell line SKOV3 induced by the Example 1, and FIG. 3H is a statistical chart of FIG. 3G after the three independent trials. In FIGS. 3B, 3D, 3F and 3H, P represents the parental primary NK cell.

Please refer to FIGS. 3A and 3B. In the control, the death rate of the human breast cancer cell line MDA-MB-231 is only about 5%. In the group 1 treated with the doxorubicin, the group 2 treated with the parental primary NK cell and the group 3 treated with the parental primary NK cell and the doxorubicin, the death rate of the human breast cancer cell line MDA-MB-231 is increased, but there is no statistically significant differences compared to the control. In the group 4 treated with the Example 1, the death rate of the human breast cancer cell line MDA-MB-231 is about 70%, and there is a statistically significant difference ($p<0.001$) compared to the group 2. Furthermore, in the group 5 treated with the Example 1 and the doxorubicin, the death rate of the human breast cancer cell line MDA-MB-231 can reach more than 80%, and there is a statistically significant difference ($p<0.05$) compared to the group 4 and a statistically significant difference ($p<0.01$) compared to the group 3, respectively.

Please refer to FIGS. 3C and 3D. In the control, the death rate of the human malignant brain tumor cell line DBTRG is less than 5%. In the group 1 treated with the temozolomide, the group 2 treated with the parental primary NK cell and the group 3 treated with the temozolomide and the parental primary NK cell, the death rate of the human malignant brain tumor cell line DBTRG is increased, but there is no statistically significant differences compared to the control. In the group 4 treated with the Example 1, the death rate of the human malignant brain tumor cell line DBTRG is more than 60%, and there is a statistically significant difference ($p<0.001$) compared to the group 2. Furthermore, in the group 5 treated with the temozolomide and the Example 1, the death rate of the human malignant brain tumor cell line DBTRG can reach about 90%, and there is a statistically significant difference ($p<0.01$) compared to the group 4 and a statistically significant difference ($p<0.001$) compared to the group 3, respectively.

Please refer to FIGS. 3E and 3F. In the control, the death rate of the human pancreatic cancer cell line AsPC1 is less than 5%. In the group 1 treated with the gemcitabine, the group 2 treated with the parental primary NK cell and the group 3 treated with the gemcitabine and the parental primary NK cell, the death rate of the human pancreatic cancer cell line AsPC1 is increased, but there is no statistically significant differences compared to the control. In the group 4 treated with the Example 1, the death rate of the human pancreatic cancer cell line AsPC1 is approximately 50%, and there is a statistically significant difference ($p<0.01$) compared to the group 2. Furthermore, in the group 5 treated with the gemcitabine and the Example 1, the death rate of the human pancreatic cancer cell line AsPC1 can reach 70%, and there is a statistically significant difference ($p<0.05$) compared to the group 4 and a statistically significant difference ($p<0.001$) compared to the group 3, respectively.

Please refer to FIGS. 3G and 3H. In the control, the death rate of the human ovarian cancer cell line SKOV3 is less than 5%. In the group 1 treated with the carboplatin and the group 2 treated with the parental primary NK cell, the death rate of the human ovarian cancer cell line SKOV3 is increased, but there is no statistically significant differences compared to the control. In the group 3 treated with the carboplatin and the parental primary NK cell, the death rate of the human ovarian cancer cell line SKOV3 can increase approximately 40%, but there is no statistically significant differences compared to the control. In the group 4 treated with the Example 1, the death rate of the human ovarian cancer cell line SKOV3 is about 60%, and there is a statistically significant difference ($p<0.05$) compared to the group 2. Furthermore, in the group 5 treated with the carboplatin and the Example 1, the death rate of the human ovarian cancer cell line SKOV3 can reach about 70%, and there is a statistically significant difference ($p<0.05$) compared to the group 4 and a statistically significant difference ($p<0.01$) compared to the group 3, respectively.

In FIGS. 3A to 3H, the results indicate that the Example 1 can be used to treat with the breast cancer cell, the glioblastoma multiforme cell, the pancreatic cancer cell or the ovarian cancer cell for excellent cell killing. Therefore, the HLA-G specific chimeric antigen receptor expressing cell of the present disclosure can be used for inhibiting the proliferation of the tumor cells in the subject in need for the treatment of the tumor. Further, the simultaneous treatment of the chemotherapy drug and the Example 1 can significantly increase the toxic effect on inducing death of the human breast cancer cell line MDA-MB-231, the human malignant brain tumor cell line DBTRG, the human pancreatic cancer cell line AsPC1 and the human ovarian cancer cell line SKOV3. The results indicate that the pharmaceutical composition for treating cancer of the present disclosure can effectively inhibit the growth of the tumor cells and treat cancer. Preferably, the pharmaceutical composition for treating cancer can include the chemotherapy drug.

2.2. Example 2

The HLA-G specific chimeric antigen receptor of the present disclosure is transduced into the primary T lymphocyte to obtain the HLA-G specific chimeric antigen receptor expressing cell of Example 2 of the present disclosure (hereinafter referred to as Example 2). The effects of the Example 2 and the pharmaceutical composition for treating cancer including the Example 2 of the present disclosure on inducing the death of the breast cancer cells, the glioblastoma multiforme cells, the pancreatic cancer cells, and the ovarian cancer cells are further demonstrated in following experiments.

First, the human breast cancer cell line MDA-MB-231, the human malignant brain tumor cell line DBTRG, the human pancreatic cancer cell line AsPC1 and the human ovarian cancer cell line SKOV3 are seeded in a 12-well plate at a density of $1 \times 10^5$ cells/well. The cells are subsequently incubated for 24 hours. Each type of the tumor cells is divided into six groups. In a control, the tumor cells are untreated. In a group 1, the tumor cells are treated with the chemotherapy drug. In a group 2, the tumor cells are treated with the parental primary T lymphocyte. In a group 3, the tumor cells are treated with the parental T lymphocyte and the chemotherapy drug. In the groups 2 and 3, the number of the parental primary T lymphocyte treated is $1 \times 10^5$ cells. In a group 4, the tumor cells are treated with the Example 2. In a group 5, the tumor cells are treated with the Example 2 and the chemotherapy drug. In the groups 4 and 5, the number of the Example 2 treated is $1 \times 10^5$ cells. The chemotherapy drug used for treating the human breast cancer cell line MDA-MB-231 is doxorubicin (200 nM), the chemotherapy drug used for treating the human malignant brain tumor cell line DBTRG is temozolomide (80 µg/mL), the chemotherapy drug used for treating the human pancreatic cancer cell line AsPC1 is gemcitabine (20 µM), and the chemotherapy drug used for treating the human ovarian cancer cell line SKOV3 is carboplatin (20 µM). The treated cells are stained with Annexin V-FITC and propidium iodide (PI), and the apoptosis and the death of the tumor cells are detected by the flow cytometry. The sum of the percentage of cells stained with Annexin V-FITC and/or PI (that is the percentage of cells in the first quadrant, the second quadrant, and the fourth quadrant of the bivariate flow cytometry scatter plot) are calculated to obtain the cytotoxicity. The results of the cytotoxicity are counted after the three independent trials in each group.

Figure 4A:
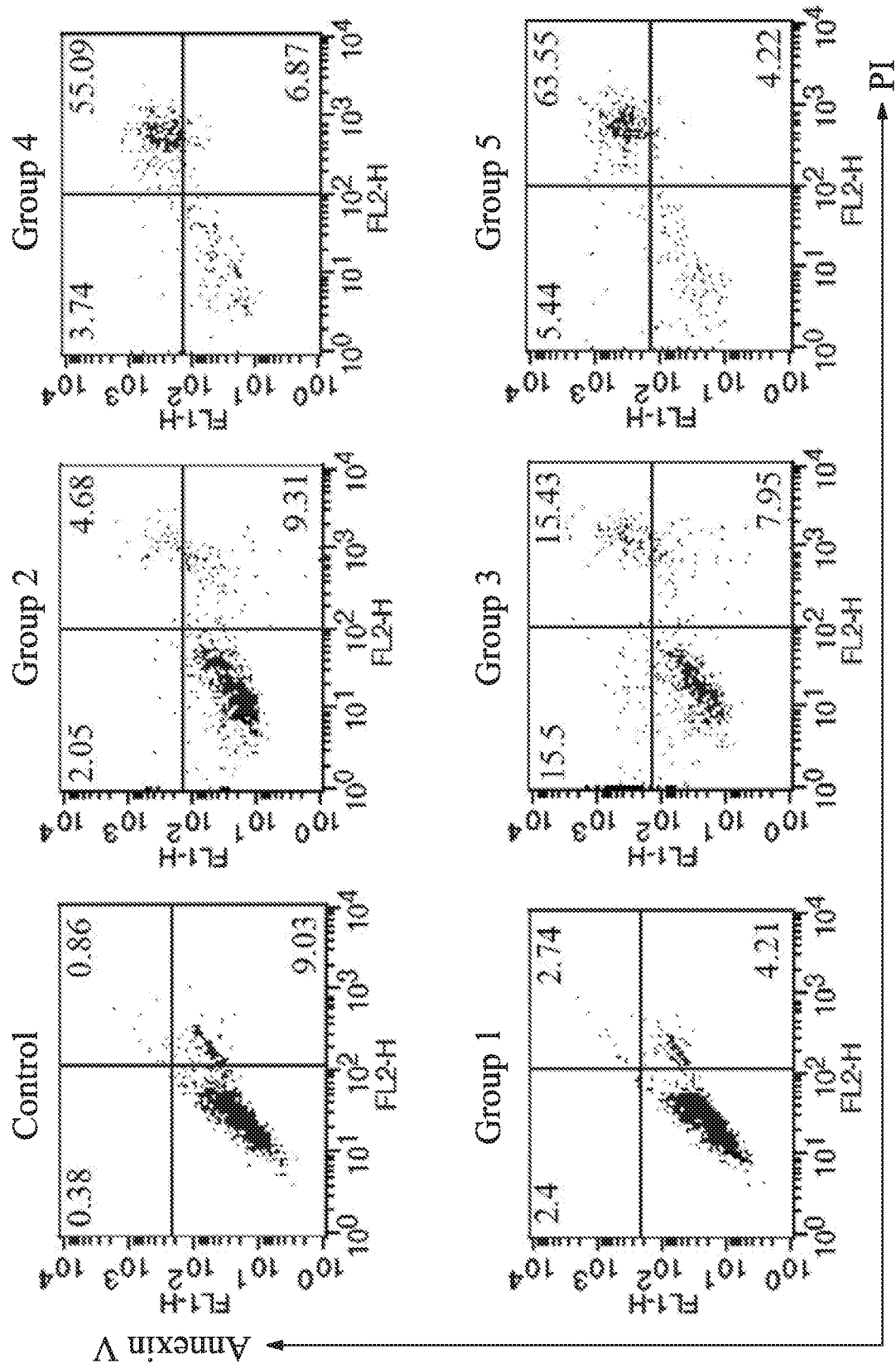
FIGS. 4A, 4B, 4C, 4D, 4E, 4F, 4G and 4H show analytical results of tumor cell death induced by HLA-G specific chimeric antigen receptor expressing cells according to Example 2 of the present disclosure.
Figure 4B:
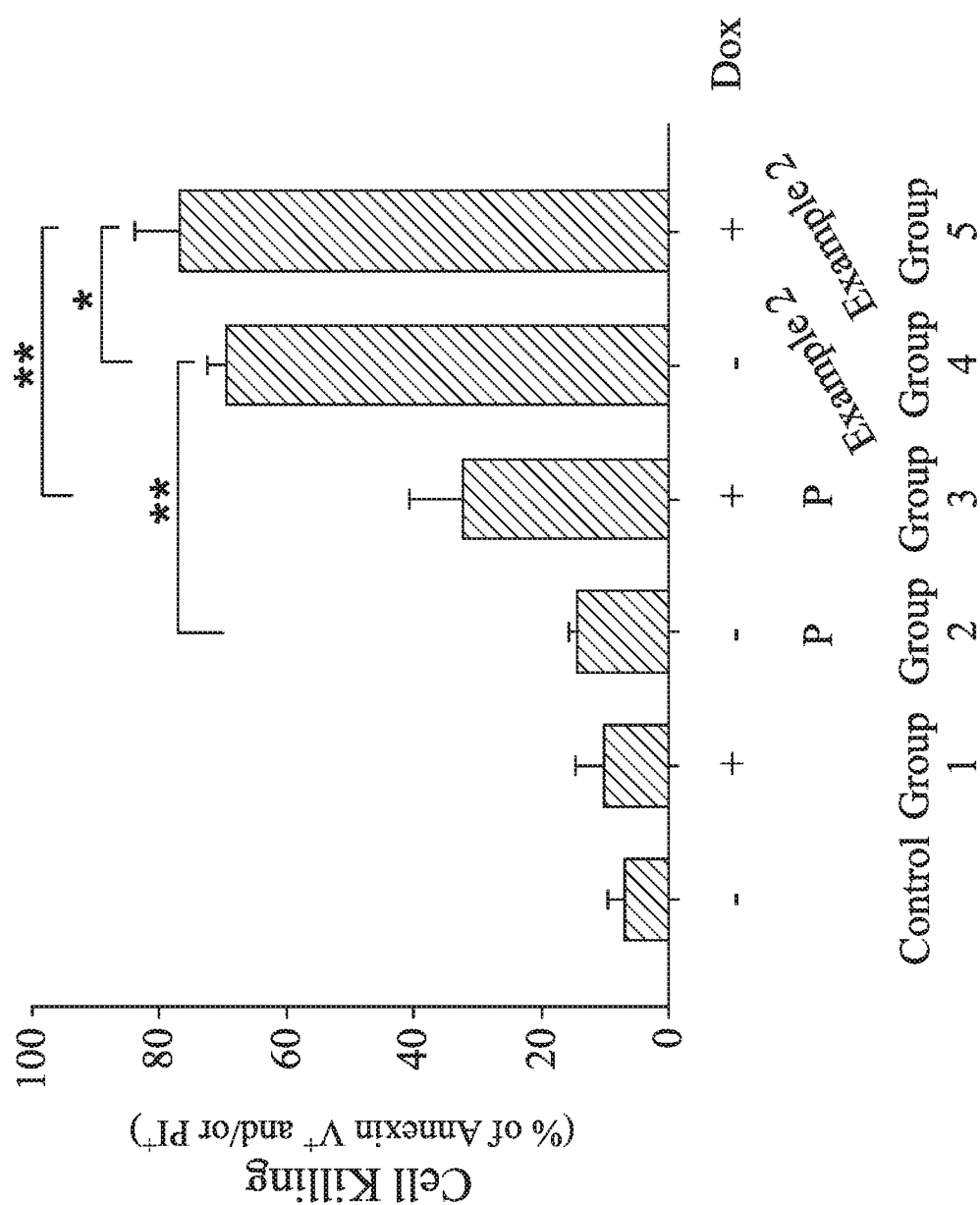
Figure 4C:
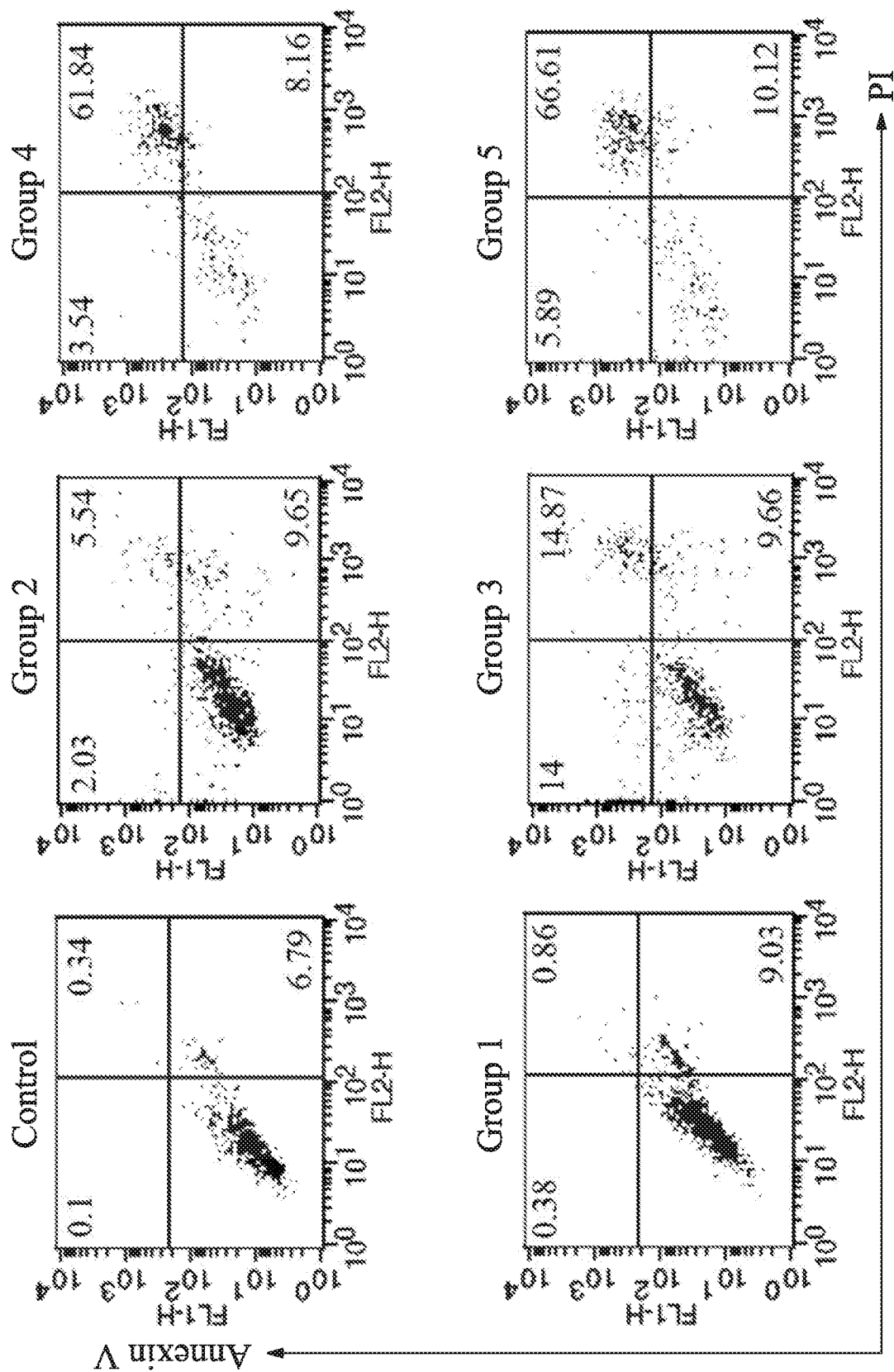
Figure 4D:
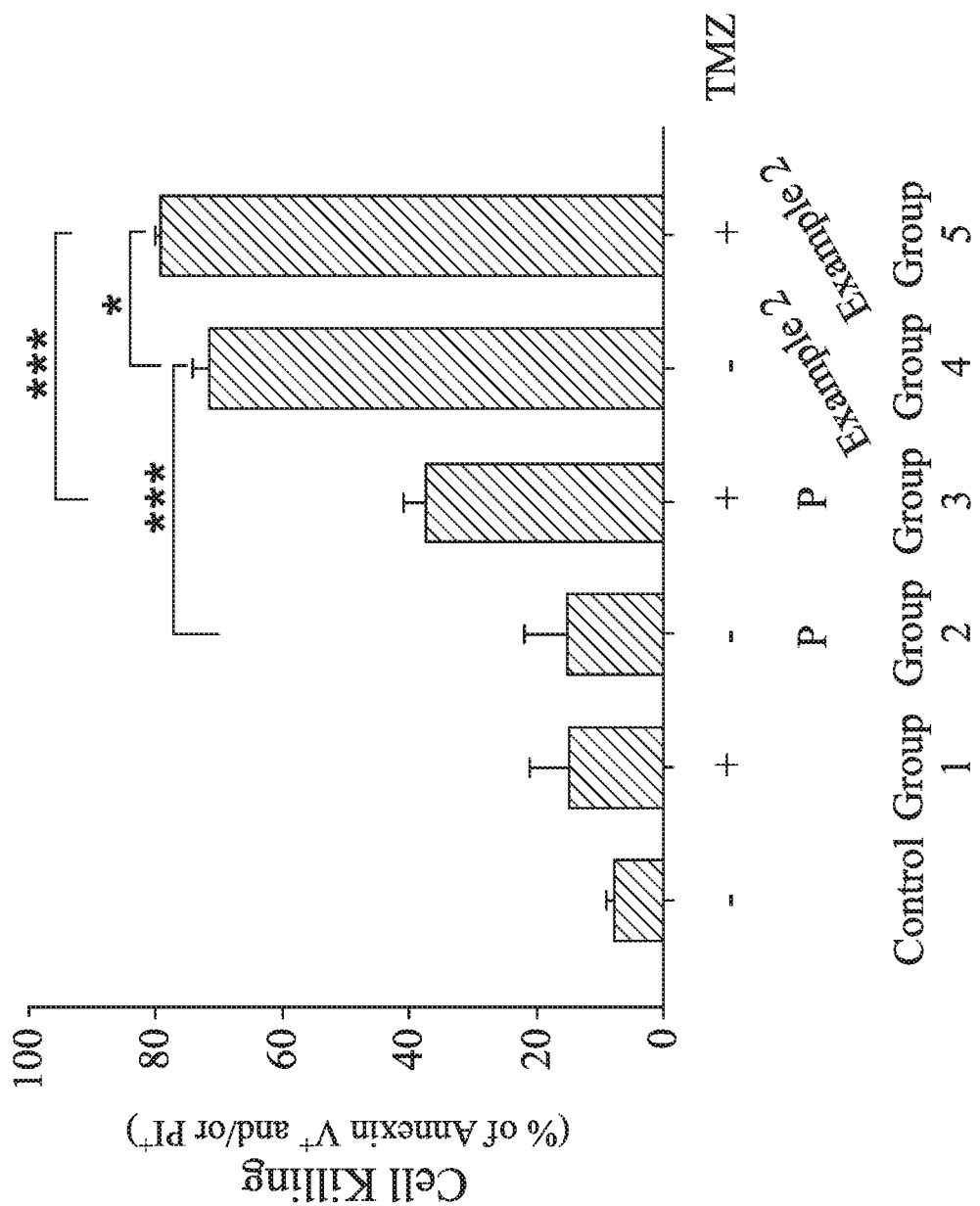
Figure 4E:
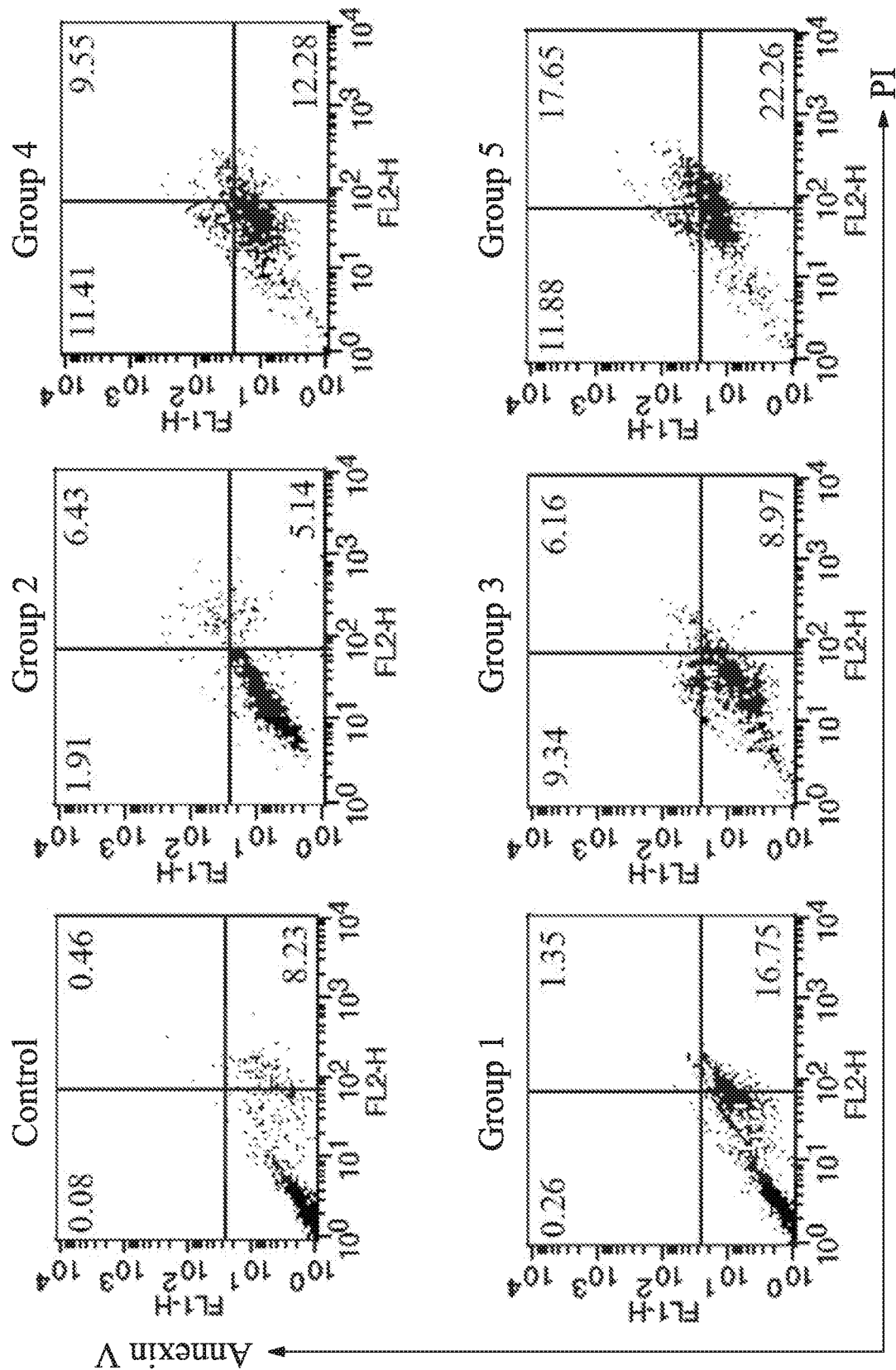
Figure 4F:
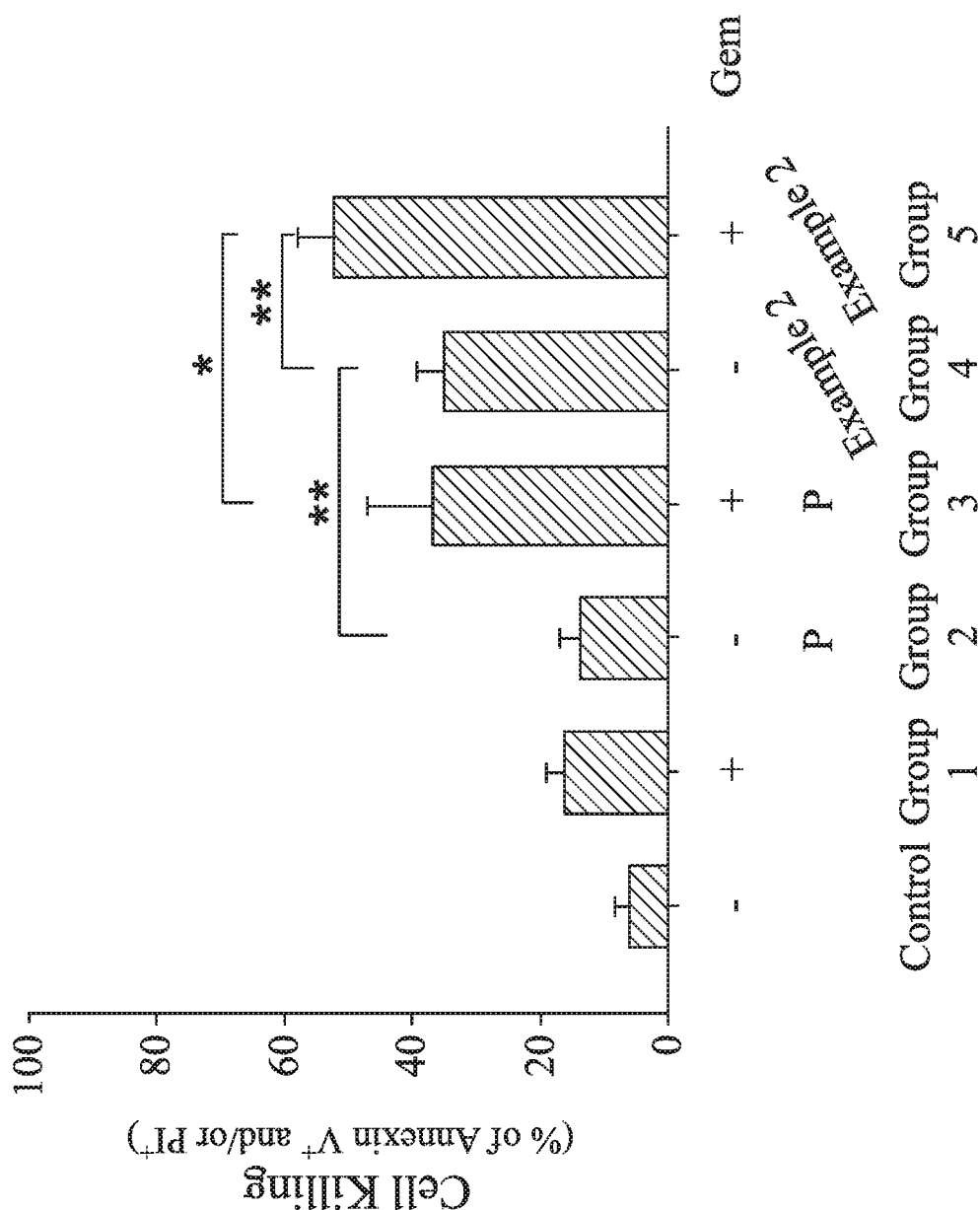
Figure 4G:
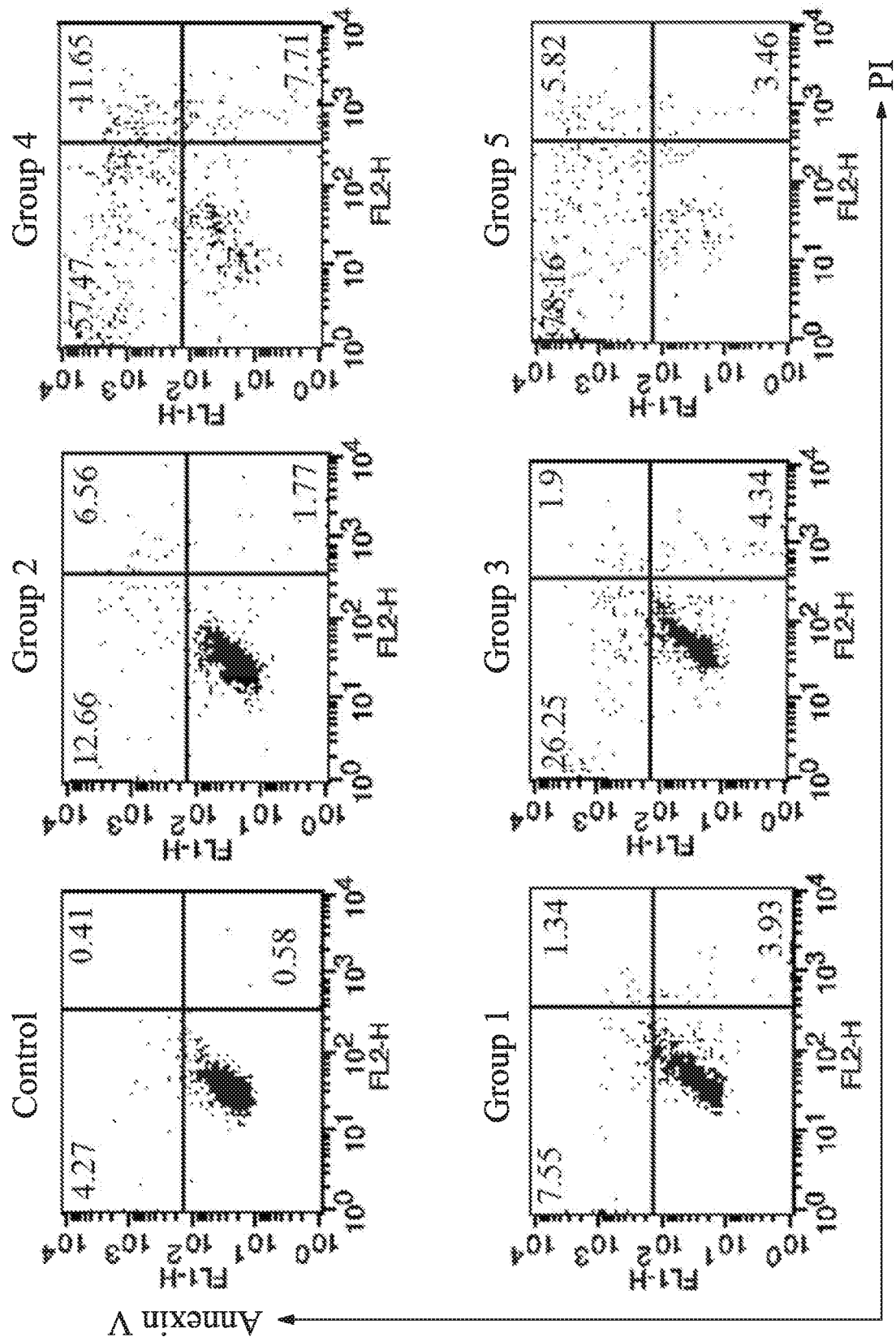
Figure 4H:
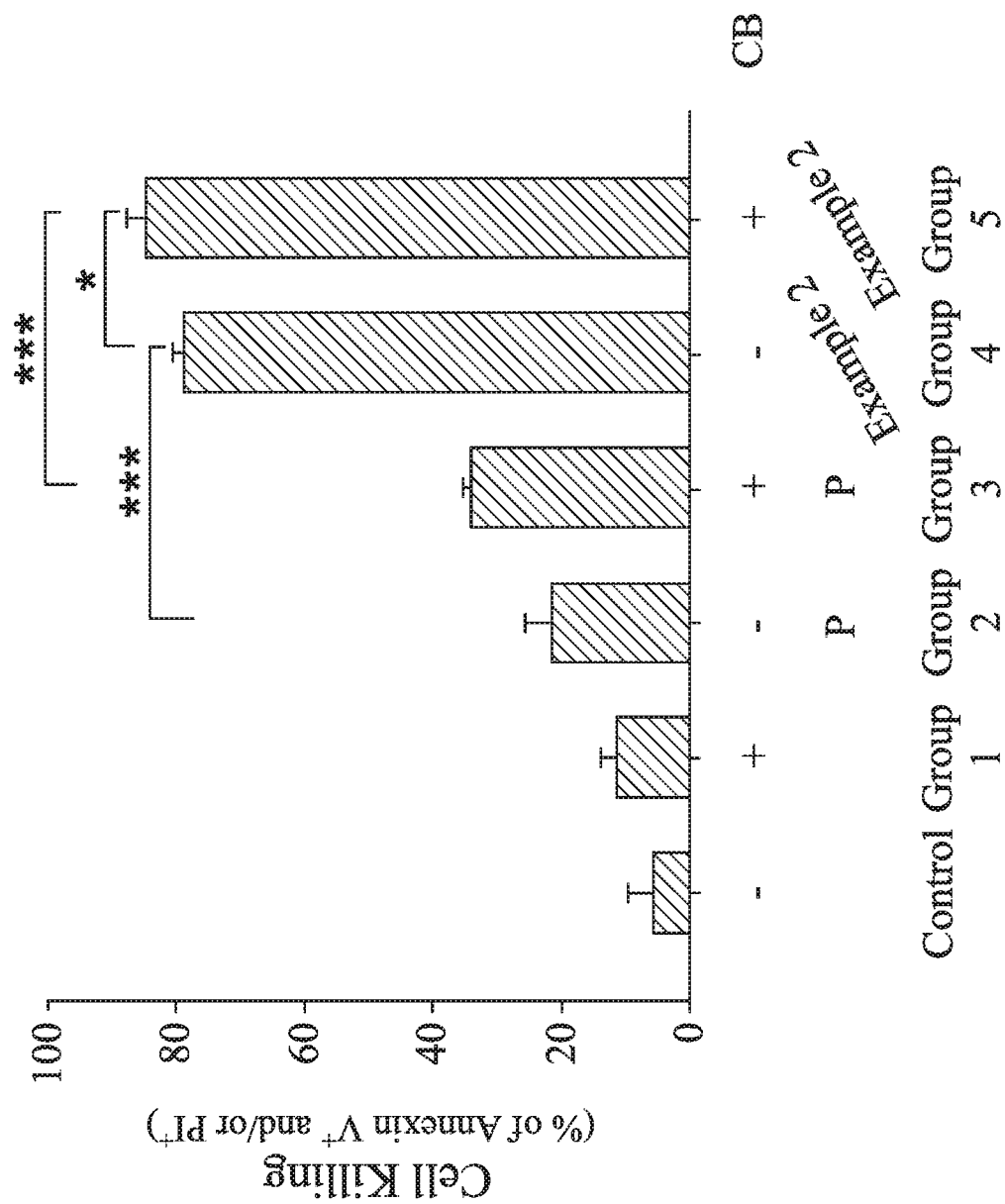

FIGS. 4A, 4B, 4C, 4D, 4E, 4F, 4G and 4H show analytical results of tumor cell death induced by the Example 2 of the present disclosure. FIG. 4A is a graph showing the analytical results of the death of the human breast cancer cell line MDA-MB-231 induced by the Example 2, and FIG. 4B is a statistical chart of FIG. 4A after the three independent trials. FIG. 4C is a graph showing the analytical results of the death of the human malignant brain tumor cell line DBTRG induced by the Example 2, and FIG. 4D is a statistical chart of FIG. 4C after the three independent trials. FIG. 4E is a graph showing the analytical results of the death of the human pancreatic cancer cell line AsPC1 induced by the Example 2, and FIG. 4F is a statistical chart of FIG. 4E after the three independent trials. FIG. 4G is a graph showing the analytical results of the death of the human ovarian cancer cell line SKOV3 induced by the Example 2, and FIG. 4H is a statistical chart of FIG. 4G after the three independent trials. In FIGS. 4B, 4D, 4F and 4H, P represents the parental primary T lymphocyte.

Please refer to FIGS. 4A and 4B. In the control, the death rate of the human breast cancer cell line MDA-MB-231 is only about 10%. In the group 1 treated with the doxorubicin, the group 2 treated with the parental primary T lymphocyte and the group 3 treated with the doxorubicin and the parental primary T lymphocyte, the death rate of the human breast cancer cell line MDA-MB-231 is increased, but there is no statistically significant difference compared to the control. In the group 4 treated with the Example 2, the death rate of the human breast cancer cell line MDA-MB-231 is approximately 70%, and there is a statistically significant difference ($p<0.01$) compared to the group 2. Furthermore, in the group 5 treated with the doxorubicin and the Example 2, the death rate of the human breast cancer cell line MDA-MB-231 can reach about 80%, and there is a statistically significant difference ($p<0.05$) compared to the group 4 and a statistically significant difference ($p<0.01$) compared to the group 3, respectively.

Please refer to FIGS. 4C and 4D. In the control, the death rate of the human malignant brain tumor cell line DBTRG is less than 10%. In the group 1 treated with the temozolomide and the group 2 treated with the parental primary T lymphocyte, the death rate of the human malignant brain tumor cell line DBTRG is increased, but there is no statistically significant difference compared to the control. In the group 3 treated with the temozolomide and the parental primary T lymphocyte, the death rate of the human malignant brain tumor cell line DBTRG can increase to about 40%, but there is no statistically significant difference compared to the control. In the group 4 treated with the Example 2, the death rate of the human malignant brain tumor cell line DBTRG is more than 70%, and there is a statistically significant difference ($p<0.001$) compared to the group 2. Furthermore, in the group 5 treated with the temozolomide and the Example 2, the death rate of the human malignant brain tumor cell line DBTRG can reach about 80%, and there is a statistically significant difference ($p<0.05$) compared to the group 4 and a statistically significant difference ($p<0.001$) compared to the group 3, respectively.

Please refer to FIGS. 4E and 4F. In the control, the death rate of the human pancreatic cancer cell line AsPC1 is about 5%. In the group 1 treated with the gemcitabine and the group 2 treated with the parental primary T lymphocyte, the death rate of the human pancreatic cancer cell line AsPC1 is increased, but there is no statistically significant difference compared to the control. In the group 3 treated with the gemcitabine and the parental primary T lymphocyte, the death rate of the human pancreatic cancer cell line AsPC1 can increase to about 40%. In the group 4 treated with the Example 2, the death rate of the human pancreatic cancer cell line AsPC1 is increased to more than 30%, and there is a statistically significant difference ($p<0.01$) compared to the group 2. Furthermore, in the group 5 treated with the gemcitabine and the Example 2, the death rate of the human pancreatic cancer cell line AsPC1 can reach more than 50%, and there is a statistically significant difference ($p<0.01$) compared to the group 4 and a statistically significant difference ($p<0.05$) compared to the group 3, respectively.

Please refer to FIGS. 4G and 4H. In the control, the death rate of the human ovarian cancer cell line SKOV3 is less than 5%. In the group 1 treated with the parental primary T lymphocyte, the group 2 treated with the parental primary T lymphocyte and the group 3 treated with the carboplatin and the parental primary T lymphocyte, the death rate of the human ovarian cancer cell line SKOV3 is increased, but there is no statistically significant difference compared to the control. In the group 4 treated with the Example 2, the death rate of the human ovarian cancer cell line SKOV3 is approximately 80%, and there is a statistically significant difference ($p<0.001$) compared to the group 2. Furthermore, in the group 5 treated with the carboplatin and the Example 2, the death rate of the human ovarian cancer cell line SKOV3 can reach more than 80%, and there is a statistically significant difference ($p<0.05$) compared to the group 4 and a statistically significant difference ($p<0.001$) compared to the group 3, respectively.

In FIGS. 4A to 4H, the results indicate that the Example 2 can be used to treat with the breast cancer cell, the glioblastoma multiforme cell, the pancreatic cancer cell or the ovarian cancer cell for excellent cell killing. Therefore, the HLA-G specific chimeric antigen receptor expressing cell of the present disclosure can be used for inhibiting the proliferation of the tumor cells in the subject in need for the treatment of the tumor. Further, the simultaneous treatment of the chemotherapy drug and the Example 2 can significantly increase the toxic effect on inducing death of the human breast cancer cell line MDA-MB-231, the human malignant brain tumor cell line DBTRG, the human pancreatic cancer cell line AsPC1 and the human ovarian cancer cell line SKOV3. The results indicate that the pharmaceutical composition for treating cancer of the present disclosure can effectively inhibit the growth of the tumor cells and treat cancer. Preferably, the pharmaceutical composition for treating cancer can include the chemotherapy drug.

2.3. Treatment of Chemotherapy Drug Increases the HLA-G Expression Level on the Plasma Membrane of Tumor Cells To investigate effect of the simultaneous treatment of the chemotherapy drug and the HLA-G specific chimeric antigen receptor expressing cell of the present disclosure on the tumor cells, the tumor cells are treated with the chemotherapy drug, and then detecting the HLA-G expression level of the tumor cells.

First, the human breast cancer cell line MDA-MB-231, the human malignant brain tumor cell line DBTRG, the human pancreatic cancer cell line AsPC1 and the human ovarian cancer cell line SKOV3 are seeded in a 6-well plate at a density of $2\times10^5$ cells/well. The cells are subsequently incubated for 24 hours. Each type of the tumor cells is divided into two groups. In a control, the tumor cells are untreated. In an experiment group, the tumor cells are treated with the chemotherapy drug for 48 hours. The chemotherapy drug used for treating the human breast cancer cell line MDA-MB-231 is doxorubicin (200 nM), the chemotherapy drug used for treating the human malignant brain tumor cell line DBTRG is temozolomide (80 μg/mL), the chemotherapy drug used for treating the human pancreatic cancer cell line AsPC1 is gemcitabine (20 μM), and the chemotherapy drug used for treating the human ovarian cancer cell line SKOV3 is carboplatin (20 μM). Then, the HLA-G expression level of the tumor cells are detected by flow cytometry.

Figure 5:
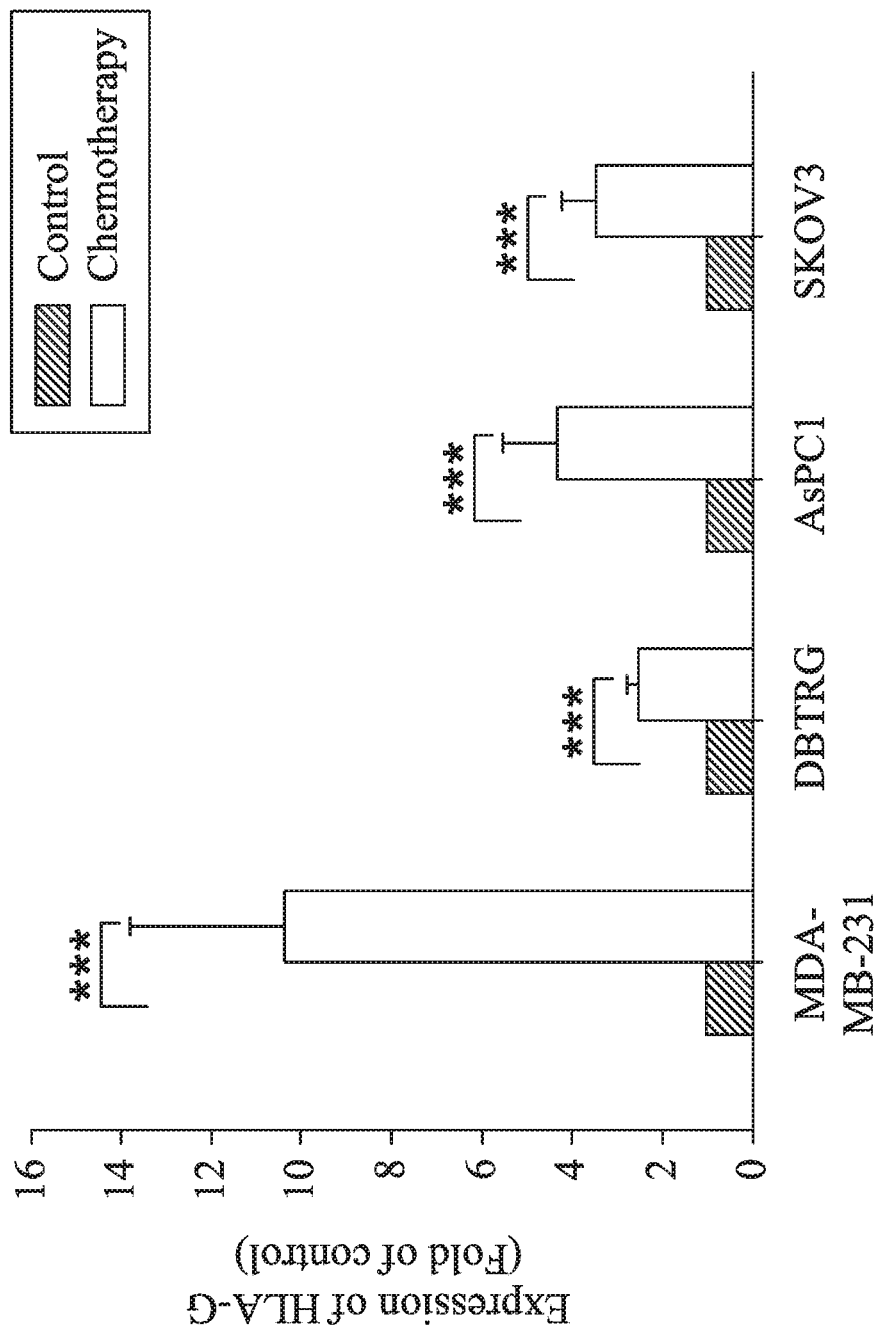
FIG. 5 is an analytical result of flow cytometry showing a HLA-G expression of tumor cells treated with a chemotherapy drug.

Please refer to FIG. 5, which is an analytical result of flow cytometry showing a HLA-G expression of tumor cells treated with a chemotherapy drug. In FIG. 5, compared to the control group of the same tumor cell and the chemotherapy group, treatment with doxorubicin can increase the expression of HLA-G on the plasma membrane of the human breast cancer cell line MDA-MB-231 ($p<0.001$), treatment with temozolomide can increase the expression of HLA-G on the plasma membrane of the human malignant brain tumor cell line DBTRG ($p<0.001$), treatment with gemcitabine can increase the expression of HLA-G on the plasma membrane of the human pancreatic cancer cell line AsPC1 ($p<0.001$), and the treatment with carboplatin can increase the expression of HLA-G on the plasma membrane of the human ovarian cancer cell line SKOV3 ($p<0.001$). The results in FIG. 5 indicate that the treatment of the chemotherapy drug can increase the HLA-G expression level on the plasma membrane of the tumor cells. Accordingly, the HLA-G specific chimeric antigen receptor expressing cell of the present disclosure can bind to the HLA-G, which is specifically recognized on the surface of the tumor cell. Therefore, the method for treating cancer of the present disclosure further administers a composition containing a plurality of HLA-G specific chimeric antigen receptor expressing cells to the subject in need for a treatment of cancer, in which the HLA-G specific chimeric antigen receptor expressing cells expresses the HLA-G specific chimeric antigen receptor specific to HLA-G, in order to enhance the effect of killing tumor cells. The treatment of the chemotherapy drug and the composition containing the HLA-G specific chimeric antigen receptor expressing cells can be in a sequence or simultaneous.

To sum up, the HLA-G specific chimeric antigen receptor of the present disclosure has excellent specific binding ability to the tumor cells, in particular, specific binding to HLA-G expressed on the plasma membrane of tumor cells. Accordingly, the HLA-G specific chimeric antigen receptor expressing cell of the present disclosure, which expresses the HLA-G specific chimeric antigen receptor of the present disclosure, can specifically target the tumor cells to avoid the off-target effect, thereby effectively killing the tumor cells. Therefore, the HLA-G specific chimeric antigen receptor expressing cell can be used for inhibiting the proliferation of the tumor cells in the subject in need for the treatment of the tumor. The pharmaceutical composition for treating the cancer includes the HLA-G specific chimeric antigen receptor expressing cell of the present disclosure and the pharmaceutically acceptable carrier, which can effectively kill tumor cells and thereby treat cancer. The pharmaceutical composition for treating the cancer further including the chemotherapy drug can increase the HLA-G expression level on the plasma membrane of tumor cells. The HLA-G specific chimeric antigen receptor expressed by the HLA-G specific chimeric antigen receptor expressing cell of the present disclosure has excellent specific binding ability to the tumor cells, especially specific binding to HLA-G expressed on the plasma membrane of tumor cells, and can specifically target the tumor cells to avoid the off-target effect, thereby effectively killing the tumor cells. Accordingly, the pharmaceutical composition for treating the cancer further including the chemotherapy drug has more excellent tumor cell toxicity.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A HLA-G specific chimeric antigen receptor, comprising, in order from an N-terminus to a C-terminus:
   an antigen recognition domain comprising a monoclonal antibody fragment specific to human leukocyte antigen G (HLA-G), wherein the antigen recognition domain comprises the amino acid sequence of SEQ ID NO: 1;
   a transmembrane domain comprising the amino acid sequence of SEQ ID NO: 2;
   an IL2 receptor β chain signaling domain comprising the amino acid sequence of SEQ ID NO: 3; and
   a CD3ζ signaling domain comprising the amino acid sequence of SEQ ID NO: 4.

2. The HLA-G specific chimeric antigen receptor of claim 1, further comprising a signal peptide comprising the amino acid sequence of SEQ ID NO: 5, wherein the signal peptide is linked to the N-terminus of the antigen recognition domain.

3. The HLA-G specific chimeric antigen receptor of claim 1, further comprising a CD8 hinge region, wherein the CD8 hinge region links the antigen recognition domain and the transmembrane domain.

4. A nucleic acid encoding the HLA-G specific chimeric antigen receptor of claim 1, comprising, in order from a 5' end to a 3' end:
   an antigen recognition domain coding fragment comprising the nucleic acid sequence of SEQ ID NO: 12;
   a transmembrane domain coding fragment comprising the nucleic acid sequence of SEQ ID NO: 13;
   an IL2 receptor β chain signaling domain coding fragment comprising the nucleic acid sequence of SEQ ID NO: 14; and
   a CD3ζ signaling domain coding fragment comprising the nucleic acid sequence of SEQ ID NO: 15.

5. The nucleic acid of claim 4, further comprising a signal peptide coding fragment comprising the nucleic acid sequence of SEQ ID NO: 16, wherein the signal peptide coding fragment is linked to the 5' end of the antigen recognition domain coding fragment.

6. The nucleic acid of claim 4, further comprising a CD8 hinge region coding fragment, wherein the CD8 hinge region coding fragment links the antigen recognition domain coding fragment and the transmembrane domain coding fragment.

7. A HLA-G specific chimeric antigen receptor expression plasmid comprising, in order from a 5' end to a 3' end:
   a promoter comprising the nucleic acid sequence of SEQ ID NO: 18; and
   the nucleic acid of claim 4.

8. A HLA-G specific chimeric antigen receptor expressing cell, comprising:
   an immune cell; and
   the HLA-G specific chimeric antigen receptor expression plasmid of claim 7.

9. The HLA-G specific chimeric antigen receptor expressing cell of the claim 8, wherein the immune cell is a T lymphocyte.

10. The HLA-G specific chimeric antigen receptor expressing cell of the claim 8, wherein the immune cell is a natural killer (NK) cell.

11. The HLA-G specific chimeric antigen receptor expressing cell of the claim 10, wherein the NK cell is a NK-92 cell line or a primary NK cell.

12. A pharmaceutical composition for treating cancer, comprising:
   the HLA-G specific chimeric antigen receptor expressing cell of claim 8; and
   a pharmaceutically acceptable carrier.

13. The pharmaceutical composition for treating cancer of claim 12, further comprising a chemotherapy drug.

14. The pharmaceutical composition for treating cancer of claim 13, wherein the chemotherapy drug is doxorubicin, temozolomide, gemcitabine or carboplatin.

15. A method for inhibiting a proliferation of a tumor cell comprising administering a composition containing a plurality of the HLA-G specific chimeric antigen receptor expressing cells of claim 8 to a subject in need for a treatment of a tumor, wherein the tumor cell expresses HLA-G on the plasma membrane thereof.

16. The method of claim 15, wherein the tumor cell is a breast cancer cell, a glioblastoma multiforme cell, a pancreatic cancer cell or an ovarian cancer cell.

\* \* \* \* \*